United States Patent
Grevious et al.

(10) Patent No.: US 9,449,501 B2
(45) Date of Patent: *Sep. 20, 2016

(54) CHOPPER MIXER TELEMETRY CIRCUIT

(71) Applicant: Medtronic, Inc., Minneapolis, MN (US)

(72) Inventors: John J. Grevious, Minneapolis, MN (US); Timothy J. Denison, Minneapolis, MN (US)

(73) Assignee: Medtronics, Inc., Minneapolis, MN (US)

( * ) Notice: Subject to any disclaimer, the term of this patent is extended or adjusted under 35 U.S.C. 154(b) by 111 days.

This patent is subject to a terminal disclaimer.

(21) Appl. No.: 14/296,206

(22) Filed: Jun. 4, 2014

(65) Prior Publication Data

US 2014/0288393 A1 Sep. 25, 2014

Related U.S. Application Data

(63) Continuation of application No. 11/799,108, filed on Apr. 30, 2007, now Pat. No. 8,781,595.

(51) Int. Cl.
*A61N 1/08* (2006.01)
*G08C 17/02* (2006.01)
(Continued)

(52) U.S. Cl.
CPC ............. *G08C 17/02* (2013.01); *A61B 5/0002* (2013.01); *A61M 5/172* (2013.01); *A61N 1/08* (2013.01); *A61N 1/37223* (2013.01); *A61N 1/37252* (2013.01); *H03F 3/393* (2013.01)

(58) Field of Classification Search
CPC ............... A61N 1/08; A61N 1/37223; A61N 1/37252; H03F 3/393; G08C 17/02; A61B 5/0003; A61B 5/0015
See application file for complete search history.

(56) References Cited

U.S. PATENT DOCUMENTS

| 1,342,885 A | 6/1920 | Armstrong |
| 3,130,373 A | 4/1964 | Braymer |

(Continued)

FOREIGN PATENT DOCUMENTS

| CN | 2754557 Y | 2/2006 |
| CN | 10199670 A | 1/2008 |

(Continued)

OTHER PUBLICATIONS

Office Action from U.S. Appl. No. 12/872,552, dated Oct. 21, 2014, 4 pp.

(Continued)

*Primary Examiner* — Tammie K Heller
(74) *Attorney, Agent, or Firm* — Shumaker & Sieffert, P.A.

(57) ABSTRACT

This disclosure describes a chopper mixer telemetry circuit for use in a wireless receiver. The receiver may be located in an implantable medical device (IMD) or external programmer. The chopper mixer telemetry circuit may include a mixer amplifier that operates as a synchronous demodulator to provide selective extraction of wireless signals received from a transmitter while suppressing out-of-band noise that can undermine the reliability of the telemetry link between an IMD or programmer and another device. The mixer amplifier may utilize parallel signal paths to convert the received telemetry signal into an in-phase (I) signal component and a quadrature (Q) signal component and recombine the I and Q signal components to reconstruct the total signal independently of the phase mismatch between the transmitter and receiver. Each signal path may include a chopper-stabilized mixer amplifier that amplifies telemetry signals within a desired band while suppressing out-of-band noise.

30 Claims, 9 Drawing Sheets

(51) Int. Cl.
- *A61N 1/372* (2006.01)
- *H03F 3/393* (2006.01)
- *A61B 5/00* (2006.01)
- *A61M 5/172* (2006.01)

(56) References Cited

U.S. PATENT DOCUMENTS

| | | |
|---|---|---|
| 3,603,997 A | 9/1971 | Brouwer |
| 3,735,274 A | 5/1973 | Nelson |
| 3,780,725 A | 12/1973 | Goldberg |
| 4,138,649 A | 2/1979 | Schaffer |
| 4,177,819 A | 12/1979 | Kofsky et al. |
| 4,188,586 A | 2/1980 | Egami |
| 4,279,258 A | 7/1981 | John |
| 4,579,125 A | 4/1986 | Strobl et al. |
| 4,610,259 A | 9/1986 | Cohen et al. |
| 4,612,934 A | 9/1986 | Borkan |
| 4,733,667 A | 3/1988 | Olive et al. |
| 4,810,960 A | 3/1989 | Owen et al. |
| 4,933,642 A | 6/1990 | Lee |
| 4,979,230 A | 12/1990 | Marz |
| 5,024,221 A | 6/1991 | Morgan |
| 5,061,593 A | 10/1991 | Yoerger et al. |
| 5,105,167 A | 4/1992 | Peczalski |
| 5,113,143 A | 5/1992 | Wei |
| 5,179,947 A | 1/1993 | Meyerson et al. |
| 5,205,285 A | 4/1993 | Baker, Jr. |
| 5,206,602 A | 4/1993 | Baumgartner et al. |
| 5,282,840 A | 2/1994 | Hudrlik |
| 5,299,569 A | 4/1994 | Wernicke et al. |
| 5,311,876 A | 5/1994 | Olsen et al. |
| 5,334,222 A | 8/1994 | Salo et al. |
| 5,458,117 A | 10/1995 | Chamoun et al. |
| 5,477,481 A | 12/1995 | Kerth |
| 5,619,536 A | 4/1997 | Gourgue |
| 5,663,680 A | 9/1997 | Nordeng |
| 5,722,052 A | 2/1998 | Abdi et al. |
| 5,725,558 A | 3/1998 | Warnke |
| 5,777,235 A | 7/1998 | Altwein |
| 5,782,884 A | 7/1998 | Stotts et al. |
| 5,843,139 A | 12/1998 | Goedeke et al. |
| 5,928,272 A | 7/1999 | Adkins et al. |
| 6,011,990 A | 1/2000 | Schultz et al. |
| 6,016,444 A | 1/2000 | John |
| 6,018,682 A | 1/2000 | Rise |
| 6,061,593 A | 5/2000 | Fischell et al. |
| 6,064,257 A | 5/2000 | Sauer |
| 6,066,163 A | 5/2000 | John |
| 6,070,101 A | 5/2000 | Struble et al. |
| 6,129,681 A | 10/2000 | Kuroda et al. |
| 6,130,578 A | 10/2000 | Tang |
| 6,161,042 A | 12/2000 | Hartley et al. |
| 6,262,626 B1 | 7/2001 | Bakker et al. |
| 6,287,263 B1 | 9/2001 | Briskin |
| 6,360,123 B1 | 3/2002 | Kimchi et al. |
| 6,456,159 B1 | 9/2002 | Brewer |
| 6,463,328 B1 | 10/2002 | John |
| 6,483,355 B1 | 11/2002 | Lee et al. |
| 6,522,914 B1 | 2/2003 | Huvelle et al. |
| 6,539,261 B2 | 3/2003 | Dal Molin |
| 6,584,351 B1 | 6/2003 | Ekwall |
| 6,597,953 B2 | 7/2003 | Boling |
| 6,617,838 B1 | 9/2003 | Miranda et al. |
| 6,621,334 B2 | 9/2003 | Ausserlechner |
| 6,625,436 B2 | 9/2003 | Tolson et al. |
| 6,667,760 B1 | 12/2003 | Limberg |
| 6,674,322 B2 | 1/2004 | Motz |
| 6,725,091 B2 | 4/2004 | Dal Molin |
| 6,753,731 B2 | 6/2004 | Maki |
| 6,754,535 B2 | 6/2004 | Noren et al. |
| 6,810,285 B2 | 10/2004 | Pless et al. |
| 6,876,842 B2 | 4/2005 | Davie |
| 6,904,321 B1 | 6/2005 | Bornzin et al. |
| 6,914,539 B2 | 7/2005 | Hoctor et al. |
| 6,952,134 B2 | 10/2005 | Burns et al. |
| 6,993,380 B1 | 1/2006 | Modarres |
| 7,006,872 B2 | 2/2006 | Gielen et al. |
| 7,010,347 B2 | 3/2006 | Schecter |
| 7,038,532 B1 | 5/2006 | Bocko et al. |
| 7,098,823 B2 | 8/2006 | O'Dowd et al. |
| 7,142,917 B2 | 11/2006 | Fukui |
| 7,146,208 B2 | 12/2006 | Holmstrom et al. |
| 7,146,218 B2 | 12/2006 | Esteller et al. |
| 7,171,258 B2 | 1/2007 | Goode |
| 7,177,609 B1 | 2/2007 | Wong |
| 7,233,198 B2 | 6/2007 | Niederkorn |
| 7,239,927 B2 | 7/2007 | Ganion |
| 7,253,685 B2 | 8/2007 | Chung |
| 7,295,061 B1 | 11/2007 | Dasgupta |
| 7,336,123 B2 | 2/2008 | Yoshida et al. |
| 7,376,463 B2 | 5/2008 | Salo et al. |
| 7,385,443 B1 | 6/2008 | Denison |
| 7,391,257 B1 | 6/2008 | Denison et al. |
| 7,504,882 B2 | 3/2009 | Saito |
| 7,595,648 B2 | 9/2009 | Ungaretti et al. |
| 7,622,988 B2 | 11/2009 | Denison et al. |
| 7,671,672 B2 | 3/2010 | McConnell |
| 7,684,867 B2 | 3/2010 | Jaax et al. |
| 7,826,894 B2 | 11/2010 | Musallam et al. |
| 7,847,628 B2 | 12/2010 | Denison |
| 8,139,015 B2 | 3/2012 | Kawaguchi et al. |
| 8,265,769 B2 | 9/2012 | Denison |
| 8,354,881 B2 | 1/2013 | Denison |
| 8,478,402 B2 | 7/2013 | Wahlstrand et al. |
| 8,781,595 B2 | 7/2014 | Grevious et al. |
| 2002/0038137 A1 | 3/2002 | Stein |
| 2002/0091332 A1 | 7/2002 | Bombardini |
| 2003/0146786 A1 | 8/2003 | Gulati et al. |
| 2004/0002635 A1 | 1/2004 | Hargrove et al. |
| 2004/0077967 A1 | 4/2004 | Jordan |
| 2004/0141558 A1 | 7/2004 | Plisch et al. |
| 2004/0158119 A1 | 8/2004 | Osorio et al. |
| 2004/0167418 A1 | 8/2004 | Nguyen et al. |
| 2005/0007091 A1 | 1/2005 | Makeig et al. |
| 2005/0081847 A1 | 4/2005 | Lee et al. |
| 2005/0118968 A1 | 6/2005 | Cowley |
| 2005/0182447 A1 | 8/2005 | Schecter |
| 2005/0282517 A1 | 12/2005 | Cowley |
| 2006/0055456 A1 | 3/2006 | Niederkorn |
| 2006/0106275 A1 | 5/2006 | Raniere |
| 2006/0116591 A1 | 6/2006 | Cooper |
| 2006/0133550 A1 | 6/2006 | Bolton et al. |
| 2006/0135877 A1 | 6/2006 | Giftakis et al. |
| 2006/0139192 A1 | 6/2006 | Morrow et al. |
| 2006/0139193 A1 | 6/2006 | Morrow et al. |
| 2006/0173501 A1 | 8/2006 | Stickney et al. |
| 2006/0184060 A1 | 8/2006 | Belalcazar et al. |
| 2006/0212089 A1 | 9/2006 | Tass |
| 2006/0241357 A1 | 10/2006 | Chirife |
| 2006/0265022 A1 | 11/2006 | John et al. |
| 2006/0281427 A1 | 12/2006 | Isaac et al. |
| 2006/0293720 A1 | 12/2006 | DiLorenzo |
| 2007/0010755 A1 | 1/2007 | Sarkela et al. |
| 2007/0016095 A1 | 1/2007 | Low et al. |
| 2007/0032737 A1 | 2/2007 | Causevic et al. |
| 2007/0077907 A1 | 4/2007 | Rector |
| 2007/0123758 A1 | 5/2007 | Miesel et al. |
| 2007/0179534 A1 | 8/2007 | Firlik et al. |
| 2007/0216477 A1 | 9/2007 | McConnell |
| 2007/0249953 A1 | 10/2007 | Frei et al. |
| 2007/0260293 A1* | 11/2007 | Carpenter ............ A61N 1/3727 607/60 |
| 2008/0015659 A1 | 1/2008 | Zhang et al. |
| 2008/0051839 A1 | 2/2008 | Libbus et al. |
| 2008/0071314 A1 | 3/2008 | John |
| 2008/0180278 A1 | 7/2008 | Denison |
| 2008/0269630 A1 | 10/2008 | Denison et al. |
| 2008/0269631 A1 | 10/2008 | Denison et al. |
| 2008/0269841 A1 | 10/2008 | Grevious et al. |
| 2009/0082691 A1 | 3/2009 | Denison et al. |
| 2010/0033240 A1 | 2/2010 | Denison et al. |
| 2010/0113964 A1 | 5/2010 | Wahlstrand et al. |

(56) References Cited

U.S. PATENT DOCUMENTS

| | | | |
|---|---|---|---|
| 2010/0324442 | A1 | 12/2010 | Blomqvist |
| 2010/0327887 | A1 | 12/2010 | Denison et al. |
| 2011/0068861 | A1 | 3/2011 | Denison |

FOREIGN PATENT DOCUMENTS

| | | | |
|---|---|---|---|
| EP | 354060 | A2 | 2/1990 |
| EP | 0568197 | A2 | 3/1993 |
| EP | 789449 | A2 | 8/1997 |
| GB | 1249395 | H | 10/1971 |
| JP | 4717841 | A | 9/1972 |
| JP | 5615112 | A | 2/1981 |
| JP | 6224659 | A | 8/1994 |
| JP | 7120207 | A | 5/1995 |
| JP | 10504099 | T | 4/1998 |
| JP | 2006279377 | A | 10/2006 |
| WO | WO9710747 | A1 | 3/1997 |
| WO | WO0201711 | A1 | 1/2002 |
| WO | WO0203087 | A1 | 1/2002 |
| WO | WO2006066098 | A1 | 6/2006 |
| WO | WO2006126186 | A2 | 11/2006 |
| WO | WO2008103078 | A1 | 8/2008 |
| WO | WO2008105692 | A1 | 9/2008 |
| WO | WO2009042172 | A2 | 4/2009 |
| WO | WO2009042313 | A1 | 4/2009 |

OTHER PUBLICATIONS

Office Action from U.S. Appl. No. 12/579,276, dated Nov. 5, 2014, 4 pp.
Response to Office Action dated Oct. 21, 2014, from U.S. Appl. No. 12/872,552, dated Jan. 21, 2015, 15 pp.
Final Office Action from U.S. Appl. No. 12/579,276, dated Mar. 10, 2015, 5 pp.
Final Office Action from U.S. Appl. No. 12/872,552, dated Mar. 12, 2015, 6 pp.
Office Action from U.S. Appl. No. 12/872,552 dated Jun. 24, 2015, 6 pp.
Notice of Allowance from U.S. Appl. No. 12/579,276, dated Jul. 17, 2015, 7 pp.
Response to Office Action dated Jul. 9, 2014, from U.S. Appl. No. 12/579,276, filed Oct. 9, 2014, 6 pp.
Abidi, "CMOS wireless transceivers: the new wave," IEEE Communications Magazine, vol. 37, Aug. 1999, pp. 119-124.
Andersen et al., "Recording Advances for Neural Prosthetics," in Engineering in Medicine and Biology Society, IEMBS 2004, 26th Annual International Conference of the IEEE, vol. 7, Sep. 1-5, 2004, pp. 5352-5355.
Andersen et al., "Selecting the signals for a brain-machine interface," Curr Opin Neurobiol, vol. 14, Dec. 2004, pp. 720-726.
Avestruz et al., "A 5 µW/Channel Spectral Analysis IC for Chronic Bidirectional Brain-Machine Interfaces," IEEE Journal of Solid-State Circuits, vol. 43(12), Dec. 2008, 19 pp.
Bakker et al., "A CMOS Nested-Chopper Instrumentation Amplifier with 1 00-nV Offset," IEEE Journal of Solid-State Circuits, vol. 35(12), Digest of Technical Papers, IEEE International, Dec. 2000, pp. 1877-1883.
Bakker, "High-Accuracy CMOS Smart Temperature Sensors," Thesis Delft University of Technology, Apr. 17, 2000, pp. 20, 21, 51 and 52.
"Baseband entry and p. 86: Authoritative Dictionary of IEEE Standard Terms (Seventh Edition)," New York: IEEE 100, 2000, 3 pp. (Note: Applicant points out in accordance with MPEP 609.04(a) that the 2000 year of publication is sufficiently earlier than the effective U.S. filing date and any foreign priority date of Apr. 30, 2007 so that the particular month of publication is not in issue.).
"Baseband entry: Academic Press Dictionary of Science and Technology," Oxford: Elsevier Science and Technology, 1992, 2 pp. (Note: Applicant points out in accordance with MPEP 609.04(a) that the 1992 year of publication is sufficiently earlier than the effective U.S. filing date and any foreign priority date of Apr. 30, 2007 so that the particular month of publication is not in issue.).
Boser, "Capacitive Interfaces for Monolithic Integrated Sensors," Chapter in RF Analog-to-Digital Converters; Sensor and Actuator Interfaces; Low-Noise Oscillators, PLLs and Synthesizers, R.J. van de Plaasche, J.H. Huijsing, and W.M.C. Sansen (eds.), Kluwer Academic Publishers, Nov. 1997, 20 pp.
Burt et al., "A Micropower Chopper-Stabilized Operational Amplifier using an SC Notch Filter with Synchronous Integration inside the Continuous-Time Signal Path," ISSCC Digest of Technical Papers, Session 19, Analog Techniques, paper 19.6, Dec. 2006, 2 pp.
Denison et al., "A 2.2µW 94nV/√JHz, Chopper-Stabilized Instrumentation Amplifier for EEG Detection in Chronic Implants" JSSC, vol. 42, No. 12, Feb. 13, 2007, pp. 2934-2945.
Denison et al., "A 2µW 100 nV/rtHz Chopper-Stabilized Instrumentation Amplifier for Chronic Measurement of Neural Field Potentials," Journal of Solid-state Circuits, IEEE Journal, vol. 42, Dec. 2007, pp. 2934-2945.
Denison et al., "An 8µW heterodyning chopper amplifier for direct extraction of 2µVrms Neuronal Brain Biomarkers," ISSCC, Feb. 5, 2008, paper 8.1, 3 pp.
Dzwonczyk et al., "Myocardial Electrical Impedance Responds to Ischemia and Reperfusion in Humans," IEEE Transactions on Biomedical Engineering, IEEE Service Center, vol. 51(12), Dec. 2004, pp. 2206-2209.
Enz et al., "Circuit Techniques for Reducing the Effects of Op-amp Imperfections: Autozeroing, Correlated Double Sampling, and Chopper Stabilization," Proceedings of the IEEE, vol. 84(11), Nov. 1996, pp. 1584-1614.
Haddad et al., "An ultra low-power dynamic translinear cardiac sense amplifier for pacemakers," Circuits and Systems, vol. 5, May 25-28, 2003 pp. V37-V40.
Haddad et al., "Analog wavelet transform employing dynamic translinear circuits for cardiac signal characterization," Circuits and Systems, vol. 1, May 2003, pp. 1-121-1-124.
Hadiashar et al., "A Chopper Stabilized CMOS Analog Multiplier with Ultra Low DC Offsets," Solid-State Circuits Conference, Sep. 2006, pp. 364-367.
Harrison et al., "A Low-Power Integrated Circuit for a Wireless 100-Electrode Neural Recording System," ISSCC Digest of Technical Papers, Session 30, Silicon for Biology, Paper 30.2, Feb. 2006, 2 pp.
Harrison et al., "A Low-Power Integrated Circuit for a Wireless 100-Electrode Neural Recording System," Solid state circuits, IEEE Journal of, vol. 42, Jan. 2007, pp. 123-133.
Harrison et al., "A Low-Power Low-Noise CMOS Amplifier for Neural Recording Applications," IEEE J. of Solid-State Circuits, vol. 38(6), Jun. 2003, pp. 958-965.
Harrison et al., "Local Field Potential Measurement with Low-Power Analog Integrated Circuit," Engineering in medicine and Biology Society, IEMBS '04, 26th Annual Conference of the IEEE, vol. 6, Sep. 1-5, 2004, pp. 4067-4070.
Heinks, "Declaration Under 37 C.F.R. 1.132," dated May 26, 2009, 4 pp.
Heinks, "Declaration Under 37 C.P.R. 1.132," by Michael W. Heinks, dated Feb. 18, 2010, 5 pp.
Hoshi, "Functional Specialization within the Dorsolateral Prefrontal Cortex: A Review of Anatomical and Physiological Studies of Non-human Primates," Neuroscience Research, vol. 54, Feb. 2006, pp. 73-84.
Jianping et al., "Study on Feature Extraction of the Sleep-Multigraph," Journal of Biomedical Engineering, vol. 22(5), Dec. 31, 2005, pp. 906-909.
Krusienski et al., "A µ-Rhythm Matched Filter for Continuous Control of a Brain-Computer Interface," Biomedical Engineering, IEEE Transactions on, vol. 54, Feb. 2007, pp. 273-280.
Kun et al., "Algorithm for Tissue Ischemia Estimation Based on Electrical Impedance Spectroscopy," IEEE Transactions on Biomedical Engineering, IEEE Service Center, vol. 50(12), Dec. 2003, pp. 1352-1359.

(56) References Cited

OTHER PUBLICATIONS

Lee et al., "A 64 Channel Programmable Closed-Loop Deep Brain Stimulator with 8 channel Neural Amplifier and Logarithmic ADC," 2008 Symposium on VLSI Circuits Digest of Technical Papers, Jun. 18-20, 2008, pp. 76-77.
Liu, "Chapter 2: Operational amplifiers," in: Demystifying Switched Capacitor Circuits, Demystifying Technology, vol. 1, May 11, 2006, pp. 15-26.
Makinwa et al., "A CMOS Temperature-to-frequency converter with an Inaccuracy of less than ±0.5° C. (3σ) from −40° C. to 105° C.," IEEE Journal of Solid State Circuits, vol. 41(12), Dec. 2006, pp. 2992-2997.
Makinwa, "Dynamic Offset-Cancellation Techniques," Electronic Instrumentation Laboratory, DIMES, Delft University of Technology, Smart Sensor Systems, 2002, 42 pp. (Note: Applicant points out in accordance with MPEP 609.04(a) that the 2002 year of publication is sufficiently earlier than the effective U.S. filing date and any foreign priority date of Apr. 30, 2007 so that the particular month of publication is not in issue.).
Martins et al., "A CMOS IC for Portable EEG Acquisition Systems," IEEE Transactions on Instrumentation and Measurement, vol. 47(5), Oct. 1998, pp. 1191-1196.
Masui, "A 0.6 V Supply CMOS Amplifier Using Noise Reduction Technique of Autozeroing and Chopper Stabilization," 21st Century COE Program, Hiroshima University, Proceedings of the Fifth Hiroshima International Workshop, Jan. 29-30, 2007, 15 pp.
Min et al., "Electrical Impedance and Cardiac Monitoring—Technology, Potential and Applications," International Journal of Bioelectromagnetism, International Society for Bioelectromagnetism, vol. 5(1), Jan. 2003, pp. 53-56.
Moualla et al., "Chopped Folded Cascade Bulk Driven OTA," Proceedings of the International Interdisciplinary Honeywell EMI, May 26, 2005, pp. 185-189.
Ng et al., "A CMOS Analog Front-End IC for Portable EEG/ECG Monitoring Applications," IEEE Trans. On Circuits and Systems, vol. 52(11), Nov. 2005, pp. 2335-2347.
Rajan et al., "Offset cancellation and 1/f noise suppression scheme for chopper amplifiers," IEEE, Circuits and Systems, vol. 1, Aug. 2002, pp. 68-71.
Rauscher, "Practical Realization of an Analyzer Operating on the Heterodyne Principle," Chapter 4 (partial) of Fundamentals of Spectrum Analysis, Rohde & Schwarz, 2001, pp. 34-64 (Note: Applicant points out in accordance with MPEP 609.04(a) that the 2001 year of publication is sufficiently earlier than the effective U.S. filing date and any foreign priority date of Apr. 30, 2007 so that the particular month of publication is not in issue.).
Rudell et al., "Recent developments in high integration multi standard CMOS transceivers for personal communication systems," Proceedings of International Symposium on Low Power Electronics and Design, The Association for Computing Machinery, Inc. (ACM), Aug. 1998, 6 pp.
Salthouse et al., "A practical micropower programmable bandpass filter for use in bionic ears," Solid-State Circuits, IEEE Journal, vol. 38(1), Jan. 2003, pp. 63-70.
Sanduleanu et al., "A Low Noise, Low Residual Offset, Chopped Amplifier for Mixed Level Applications," IEEE, Electronics, Circuits and Systems, Sep. 1998, pp. 333-336.
Sarpeshkar et al., "An ultra-low-power programmable analog bionic ear processor," Biomedical Engineering, IEEE Transactions, vol. 52, Apr. 2005, pp. 711-727.
Sarpeshkar et al., "Low power circuits for brain-machine interfaces," IEEE Transactions on Biomedical Circuits and Systems, vol. 2(3), Sep. 2008, pp. 173-183.
Sarpeshkar, "Borrowing from biology makes for low-power computing," IEEE Spectrum, May 2006, pp. 24-29.
Smart et al., "Automatic Detection of High Frequency Epileptiform Oscillations from Intracranial EEG Recordings of Patients with Neocortical Epilepsy," in Technical, Professional and Student Development Workshop, IEEE Region 5 and IEEE Denver Section, Apr. 7-8, 2005, pp. 53-58.
Wattanapanitch et al., "An energy-efficient micropower neural recording amplifier," Biomedical Circuits and Systems, IEEE Transactions, vol. 1(2), Jun. 2007, pp. 136-147.
Wu et al., "A 1V 2.3μW Biomedical Signal Acquisition IC," ISSCC Digest of Technical Papers, Session 2, Biomedical Systems, paper 2.7, Feb. 2006, 2 pp.
Yates et al., "An ultra low power low noise chopper amplifier for wireless EEG," In 49th IEEE International Midwest Symposium on Circuits and Systems, MWSCAS '06., vol. 2, Aug. 2006, 4 pp.
Yazicioglu et al., "A 200μW Eight-Channel Acquisition ASIC for Ambulatory EEG Systems," Solid-State Circuits Conference, Feb. 5, 2008, 3 pp.
Yazicioglu et al., "A 60uW 60nV/rtHz Readout Front-End for Portable Biopotential Acquisition Systems," ISSCC Digest of Technical Papers, Session 2, Biomedical Systems, paper 2.6, Feb. 2006, 2 pp.
Ying, "Chopper Stabilized Amplifiers," Term Paper, Department of Electrical and Computer Engineering, University of Toronto, Nov. 2001, 17 pp.
International Preliminary Report on Patentability from Counterpart International Patent Application No. PCT/US2007/010383, dated Nov. 23, 2009, 8 pp.
International search Report and Written Opinion from Counterpart International Patent Application No. PCT/US2007/010383, dated Mar. 18, 2008, 12 pp.
Prosecution History from U.S. Pat. No. 8,781,595, dated Sep. 14, 2012 through Jun. 13, 2014, 95 pp.
Prosecution History from U.S. Pat. No. 8,265,769, dated Nov. 9, 2011 through Jul. 2, 2012, 173 pp.
Prosecution History from U.S. Pat. No. 7,385,443, dated Sep. 24, 2007 through Feb. 19, 2008, 40 pp.
Prosecution History from U.S. Pat. No. 7,847,628, dated Apr. 7, 2010 through Jul. 29, 2010, 15 pp.
Prosecution History from U.S. Pat. No. 8,354,881, dated Mar. 15, 2011 through Oct. 9, 2012, 44 pp.
Prosecution History from U.S. Pat. No. 7,391,257, dated Sep. 20, 2007 through Apr. 28, 2008, 52 pp.
Prosecution History from U.S. Pat. No. 7,622,988, dated Dec. 24, 2008 through Jul. 7, 2009, 21 pp.
Prosecution History from U.S. Appl. No. 12/579,276, dated Jul. 19, 2011 through Jul. 9, 2014, 106 pp.
Prosecution History from U.S. Appl. No. 12/872,552, dated Jan. 15, 2013 through Aug. 7, 2014, 90 pp.
Response to Office Action dated Nov. 5, 2014, from U.S. Appl. No. 12/579,276, dated Jan. 27, 2015, 5 pp.
Office Action from U.S. Appl. No. 12/872,552, dated May 2, 2016, 5 pages.

* cited by examiner

CHOPPER MIXER TELEMETRY CIRCUIT

This application is a continuation of U.S. application Ser. No. 11/799,109, filed Apr. 30, 2007 and issued as U.S. Pat. No. 8,781,595 on Jul. 15, 2014, the entire content of which is incorporated herein by this reference.

TECHNICAL FIELD

The invention relates to wireless telemetry and, more particularly, short-range wireless telemetry.

BACKGROUND

Wireless telemetry is used to support two-way communication between an IMD, such as an implantable pulse generator (IPG), implantable drug delivery device, or implantable sensing device, and another device, such as another IMD, an external medical device, or an external programmer, such as a patient or clinician programmer. For example, an external programmer may transmit information specifying adjustment of therapy parameters or operational features of the IMD. The transmitted information may include adjustments to therapy parameters, such as electrical stimulation pulse amplitude, pulse width, pulse rate, or duration, or drug delivery dosage, drug delivery rate, dosage limits, lockout intervals, or the like. In addition, transmitted information may include entire therapy programs, including parameter sets. Also, an IMD may transmit information to another IMD, an external medical device, or an external programmer, such as operational data, status data, diagnostic data, fault data, sensor data, or the like. Reliable telemetry is an important aspect of overall operation of an IMD.

SUMMARY

This disclosure describes a chopper mixer telemetry circuit for use in a wireless receiver. The receiver may be located in an implantable medical device (IMD) or external programmer. The chopper mixer telemetry circuit may include a mixer amplifier that operates as a synchronous demodulator to provide selective extraction of wireless signals received from a transmitter while suppressing out-of-band noise that can undermine the reliability of the telemetry link between an IMD or programmer and another device. The mixer amplifier may utilize parallel signal paths to convert the received telemetry signal into an in-phase (I) signal component and a quadrature (Q) signal component and recombine the I and Q signal components to reconstruct the total signal independently of the phase mismatch between the transmitter and receiver. Each signal path may include a chopper-stabilized mixer amplifier that amplifies telemetry signals within a desired band while suppressing out-of-band noise.

In one embodiment, the disclosure provides a wireless receiver comprising a first mixer amplifier and a second mixer amplifier. The first mixer amplifier amplifies a telemetry signal modulated at a clock frequency to produce a first amplified signal, demodulates the first amplified signal at the clock frequency to produce a first demodulated signal, and extracts a portion of the first demodulated signal to produce a first output signal. The second mixer amplifier amplifies the telemetry signal to produce a second amplified signal, demodulates the second amplified signal at the clock frequency to produce a second demodulated signal that is approximately 90 degrees out of phase with the first demodulated signal, and extracts a portion of the second demodulated signal to produce a second output signal. The wireless receiver further comprises a first modulator that modulates an amplitude of the first output signal at the clock frequency, a second modulator that modulates an amplitude of the second output signal at the clock frequency, a first feedback path that applies the first modulated output signal as a first feedback signal to the first mixer amplifier, a second feedback path that applies the second modulated output signal as a second feedback signal to the second mixer amplifier, and circuitry that combines the first and second output signals to produce a third output signal.

In another embodiment, the disclosure provides a method comprising receiving a wireless, modulated telemetry signal, amplifying the modulated telemetry signal to produce a first amplified signal, demodulating the first amplified signal at a clock frequency to produce a first demodulated signal, extracting a portion of the first demodulated signal to produce a first output signal, amplifying the modulated telemetry signal to produce a second amplified signal, demodulating the first amplified signal at the clock frequency to produce a second demodulated signal that is 90 degrees out of phase with the first demodulated signal, extracting a portion of the second demodulated signal to produce a second output signal, modulating an amplitude of the first output signal at the clock frequency to produce a first modulated output signal, modulating an amplitude of the second output signal at the clock frequency to produce a second modulated output signal, applying the first modulated output signal as a first feedback signal to the modulated, differential telemetry signal, applying the second modulated output signal as a second feedback signal to the modulated, differential telemetry signal, and combining the first and second output signals to produce a third output signal.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
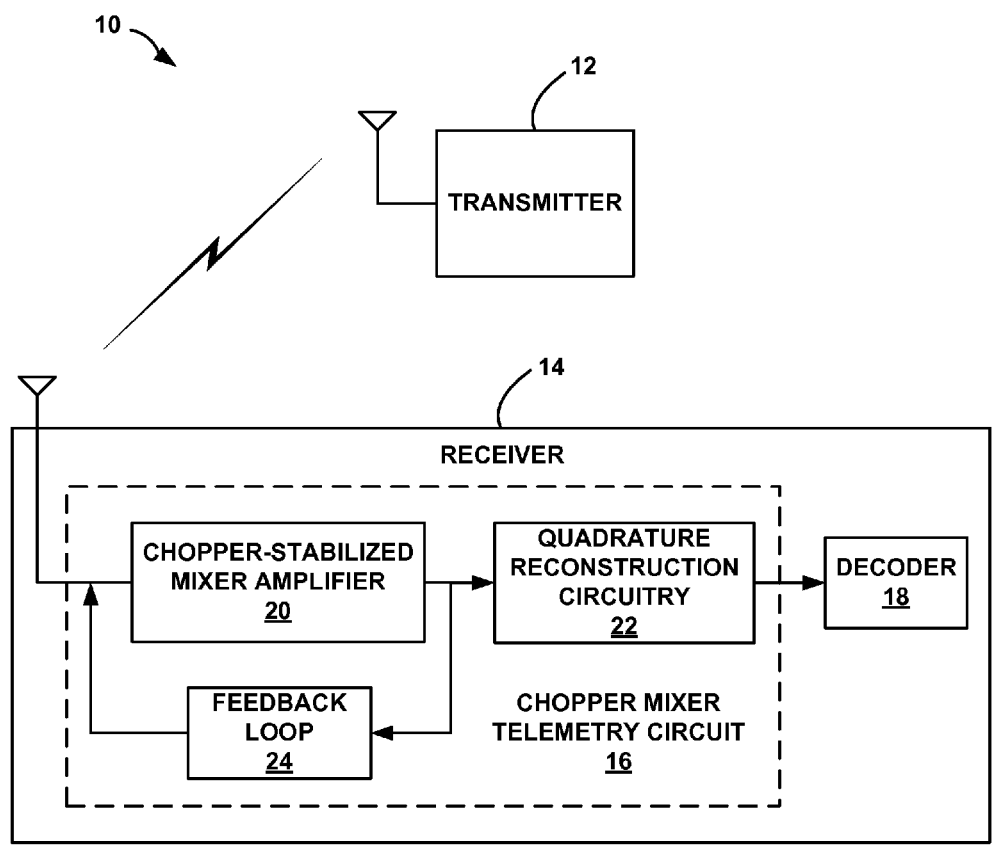
FIG. 1 is a block diagram illustrating a wireless communication system including a receiver that incorporates a chopper mixer telemetry circuit configured to support wireless telemetry.

Wireless telemetry is used to transfer data between an implantable medical device (IMD) and another device, such as another IMD, an external medical device, or an external programmer. Example IMDs include implantable pulse generators (IPGs), implantable drug delivery devices, implantable sensing devices, and the like. External programmers for an IMD include, for example, a patient or clinician programmer. External medical devices may include external therapy or sensing devices that communicate with an external programmer and/or an IMD.

An external programmer may transmit information specifying adjustment of therapy parameters or operational features of the IMD. The transmitted information may include adjustments to therapy parameters, such as electrical stimulation pulse amplitude, pulse width, pulse rate, or duration, or drug delivery dosage, drug delivery rate, dosage limits, lockout intervals, or the like. In addition, transmitted information may include entire therapy programs, including parameter sets. Also, an IMD may transmit information to another IMD, an external medical device, or an external programmer, such as operational data, status data, diagnostic data, fault data, sensor data, or the like. Reliable telemetry is an important aspect of overall operation of an IMD.

Telemetry between an IMD and external programmer may be performed at distances of approximately 5 centimeters (cm) or less. In this case, communication ordinarily requires placing the programmer on the skin of the patient directly over the IMD. Correctly positioning the programmer relative to the IMD can take time and be an inconvenience to the patient. A wireless receiver, in accordance with some embodiments of this disclosure may be configured to permit reliable telemetry operation at distances of greater than approximately 5 cm. As an example, IMDs and programmers incorporating a wireless receiver, as described in this disclosure, may provide reliable communication at distances of greater than or equal to approximately 5 cm, greater than or equal to approximately 10 cm, greater than or equal to approximately 50 cm, or at distances between approximately 5 cm and approximately 1 meter (m), between approximately 10 cm and approximately 1 m, or between approximately 50 cm and approximately 1 m. Effective, but less reliable, communication may be supported for greater distances between an IMD and another device, e.g., up to approximately 4 m, depending on antenna size, data rate, and local noise sources, and given micropower considerations.

Wireless telemetry at distances on the order of 5 cm to 1 m may generally be referred to as "arms length telemetry" (ALT), and may eliminate the burden of placing the programmer directly over the IMD. ALT may be considered short-range telemetry, given the distances described in this disclosure. Extending the distance between the IMD and programmer may require the use of telemetry circuits capable of reliably detecting telemetry signals with very low signal levels. The level of a telemetry signal tends to decrease as a cubic power of distance between the IMD and programmer, i.e., between the transmitter and receiver. As an example, signal levels for ALT may be on the order of hundreds of millivolts (mV) to hundreds of microvolts (μV).

This disclosure describes various embodiments of a chopper mixer telemetry circuit for use as a receiver in a communication system that operates with very low signal power levels over distances greater than 5 cm. Hence, the chopper mixer telemetry circuit may be useful for an ALT communication system for telemetry between an IMD and another device such as an external programmer for programming and/or interrogating the IMD. The IMD may be characterized by finite power resources that are required to last several months or years. Accordingly, to promote device longevity, IMD circuitry, such as sensing and therapy circuitry, is generally designed to consume very small levels of power. Likewise, the telemetry circuit described in this disclosure also may be designed to consume very small levels of power.

As an example, in some embodiments, operation of a chopper mixer telemetry circuit may be supported by a supply current of less than 2.0 microamps, and more preferably less than 1.0 microamp. In some embodiments, the telemetry circuit may consume supply current in a range of approximately 100 nanoamps to 1.0 microamps. Accordingly, the telemetry circuit may generally be referred to as a micropower circuit. Although medical devices are described for purposes of illustration, the described micropower telemetry circuit may be used in a variety of medical and non-medical wireless communication applications. In each case, the chopper mixer telemetry circuit may be incorporated in a receiver required to draw very low power while providing a substantially linear output and operating at a telemetry distance of greater than or equal to approximately 5 cm, greater than or equal to approximately 10 cm, greater than or equal to approximately 50 cm, or at distances between approximately 5 cm and approximately 1 meter (m), between approximately 10 cm and approximately 1 m, or between approximately 50 cm and approximately 1 m.

A chopper mixer telemetry circuit, in accordance with some embodiments of this disclosure, may include a linear, low offset, chopper-stabilized mixer amplifier that operates as a synchronous demodulator to provide selective extraction of wireless telemetry signals received from a transmitter while suppressing out-of-band noise. Examples of out-of-band noise include magnetic fields induced by stimulation currents in an IMD, cathode ray tubes, and other unwanted signals that can undermine the reliability of the telemetry link between the IMD and an external programmer.

A chopper mixer telemetry circuit, in accordance with various embodiments of this disclosure, may utilize parallel signal paths to convert a received telemetry signal into an in-phase (I) signal component and a quadrature (Q) signal component and recombines the I and Q signal components to reconstruct the total signal independently of the phase mismatch between the transmitter and receiver. Each signal path may include a chopper-stabilized mixer amplifier that amplifies telemetry signals within a desired band while suppressing out-of-band noise. Chopper stabilization may be used to substantially eliminate noise and offset from an output signal produced by the mixer amplifier. Dynamic limitations that could result from chopper stabilization at low power can be substantially eliminated through a combination of chopping at low impedance nodes within the amplifier and feedback to reduce glitching.

It may be desirable for the chopper mixer telemetry circuit to provide a substantially linear output over a very large signal range while suppressing out-of-band aggressors. For example, the chopper mixer telemetry circuit may be configured to provide a substantially linear output over a signal range of approximately 60 to 100 dB, and more particularly approximately 80 dB. It also may be desirable that the chopper mixer telemetry circuit to operate with low power in order to conserve limited battery resources and thereby promote operational longevity, particularly within an IMD having finite power resources. As mentioned above, it is also generally desirable to provide a chopper mixer telemetry circuit capable of reliable telemetry at distances of greater than or equal to approximately 5 cm, greater than or equal to approximately 10 cm, greater than or equal to approximately 50 cm, or at distances between approximately 5 cm and approximately 1 meter (m), between approximately 10 cm and approximately 1 m, or between approximately 50 cm and approximately 1 m.

FIG. 1 is a block diagram illustrating a wireless communication system 10 including a transmitter 12 and a receiver 14 configured for arms length telemetry (ALT). System 10 may be used, for example, as an ALT system operating at relatively low frequencies and low power. Receiver 14 may be located in a patient or clinician programmer or an IMD, such as an implantable pulse generator (IPG), an implantable drug delivery device, or an implantable sensing device. The IMD may be implanted within a patient and communicate, via wireless radio frequency (RF) telemetry, with the clinician or patient programmer, with an external medical device or with another IMD. In a reciprocal manner, transmitter 12 may be located in the corresponding remote device, e.g., a programmer when receiver 14 is located in an IMD and an IMD when receiver 14 is located in a programmer. Alternatively, transmitter 12 or receiver 14 may be located within another device, such as another IMD or an external medical therapy or sensing device. Receiver 14 and transmitter 12 form a telemetry system that makes use of a chopper mixer telemetry circuit having a chopper mixer amplifier 20 in accordance with various embodiments of this disclosure.

In general, system 10 may be configured for ALT, which refers to reliable telemetry at distances of greater than or equal to approximately 5 cm, greater than or equal to approximately 10 cm, greater than or equal to approximately 50 cm, or greater than or equal to approximately 100 cm. ALT generally eliminates the burden of placing a programming device directly over an IMD for communication. However, the signal level of an ALT signal may be on the order of hundreds of microvolts as a result of the signal level dropping off as a cubic power of distance between the programming device and the IMD. Consequently, ALT requires highly sensitive telemetry circuitry to extract the transmitted signal while suppressing or rejecting out of band aggressors, i.e., noise.

Transmitter 12 may be configured to transmit telemetry signals at a frequency in a range of approximately 10 kHz to 1 GHz, and more particularly in a range of approximately 150 kHz to 200 kHz for biomedical applications. In an example embodiment, telemetry signals produced by transmitter 12 may be on-off-keyed (OOK) signals in the 175 kHz industrial-scientific-medical (ISM) band with a 4.4 kilobits per second (kbps) data transmission rate. Such telemetry signals are representative of those that may be used for wireless telemetry for an IMD. However, such telemetry signals are described for purposes of example and illustration and should not be considered limiting of various aspects of a chopper mixer telemetry circuit, as broadly embodied and described in this disclosure.

Data carried by the telemetry signals may be framed with a fixed interval of 228 µs to provide a 4.4 kbps rate. The duty cycle of the signal within the frame represents whether the data bit is a one or a zero. It should be understood that system 10 is not limited to the above protocol. Instead, this protocol is one of many example protocols that may be used for ALT. Accordingly, system 10 should be viewed as an example to illustrate mixer amplifier 20 for synchronous demodulation of signals for ALT and, therefore, should not be considered limiting in any way.

As shown in FIG. 1, receiver 14 includes a chopper mixer telemetry circuit 16 and a decoder 18. In the example of FIG. 1, chopper mixer telemetry circuit 16 includes a chopper-stabilized mixer amplifier 20, quadrature reconstruction circuitry 22, and feedback path 24. Receiver 14 and, more particularly, chopper mixer telemetry circuit 16 may be configured to operate as a synchronous demodulator that provides selective extraction of the received telemetry signal while suppressing out-of-band aggressors. In general, chopper-stabilized mixer amplifier 20 amplifies the received telemetry signal and demodulates the amplified signal from the carrier frequency to baseband. During this process, noise that enters the signal path of amplifier 20, i.e., 1/f noise, popcorn noise, and offset, is modulated up to the carrier frequency. However, the desired signal, which has already been mixed up to the carrier frequency at the transmitter, is mixed down to baseband. In addition, other out-of band noise, such as induced electromagnetic interference, is up-converted out of the baseband. In this manner, amplifier 20 segregates the desired baseband signals from the up-converted noise signals and substantially reduces or eliminates components located at the carrier frequency, i.e., the 1/f noise, popcorn noise, and offset. In this way, amplifier 20 provides a low noise output.

Figure 4:
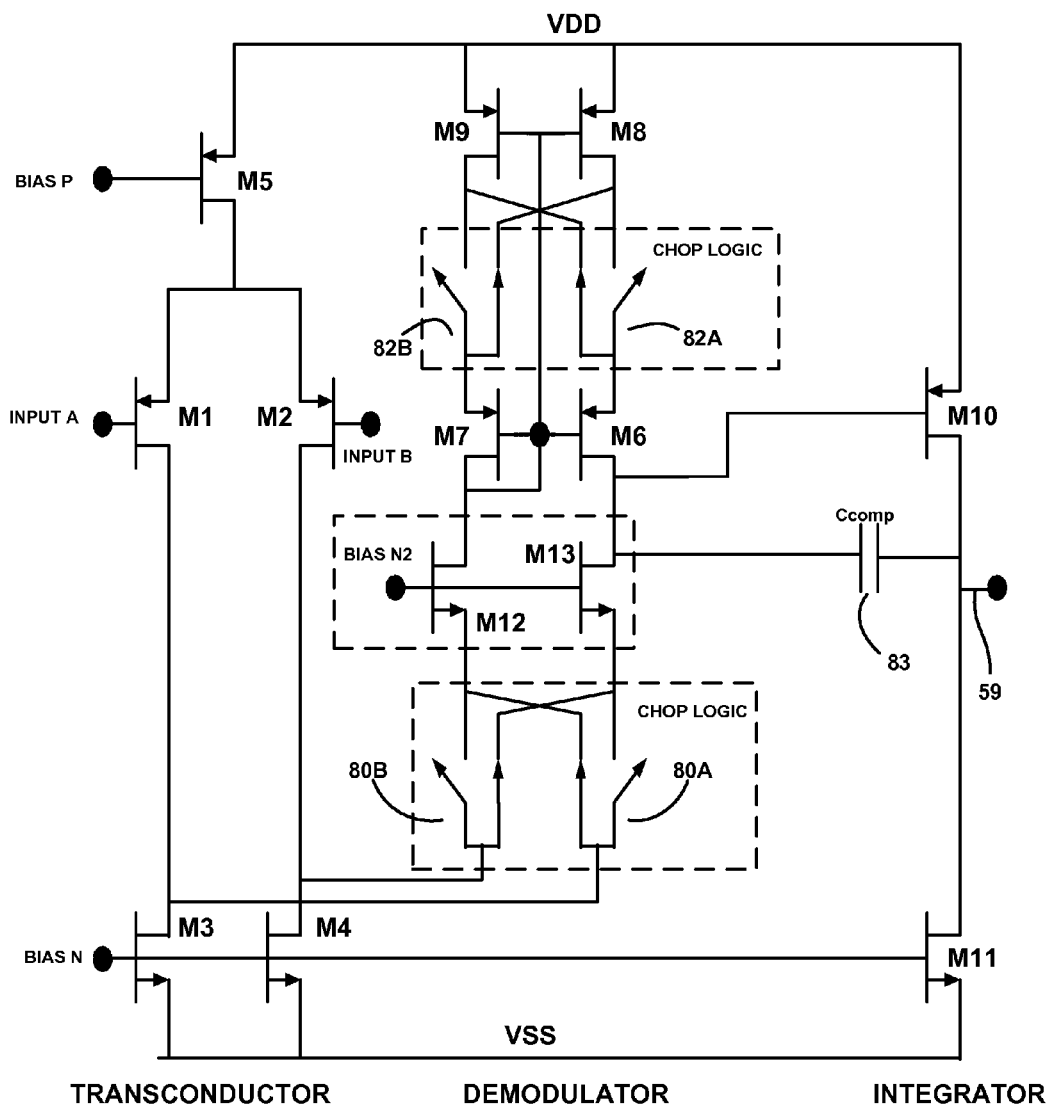
FIG. 4 is a circuit diagram illustrating a chopper-stabilized mixer amplifier that may be used to form part of the chopper mixer telemetry circuit

Mixer amplifier 20 demodulates the received telemetry signal by converting the received signal into an in-phase (I) signal component and a quadrature (Q) signal component using parallel signal paths. As described in this disclosure, each of the parallel signal paths of amplifier 20 uses chopper stabilization to substantially eliminate noise and offset from the respective I or Q output signal and includes an amplifier, a chopper, and an integrator. The amplifier, chopper, and integrator may be implemented as an amplifier that has a modified folded cascode architecture that provides switching, e.g., via CMOS switches, at low impedance nodes, e.g., as shown in FIG. 4. Switching at low impedance node enables chopping at higher frequencies where the only limitation would be the charge injection offset.

In general, amplifier 20 may have limited bandwidth because it operates under the constraints of a micropower system, e.g., within an IMD having limited power resources The limited bandwidth can cause glitching, i.e., ripple or spikes, in the output signal. For this reason, feedback loop 24 may be coupled between the output and input of mixer amplifier 20. Feedback loop 24 provides negative feedback to keep the signal changes at the input to mixer amplifier 20 relatively small. More particularly, feedback loop 24 keeps changes at the inputs to the amplifiers of each of the parallel chopper-stabilized signal paths relatively small. Feedback loop 24 may have a differential configuration that substantially eliminates glitching in the output of amplifier 20 by driving the net input signal to mixer amplifier 20 toward zero. In this way, feedback loop 24 keeps the signal change at the input of mixer amplifier 20 relatively small in steady state. As a result, mixer amplifier 20 achieves a stable, low noise, low distortion output while operating at low power.

Quadrature reconstruction circuitry 22 uses the output of the parallel signal paths, i.e., the I and Q signal components, to reconstruct the total signal independent of the phase mismatch between transmitter 12 and receiver 14. Decoder 18 converts the reconstructed signal, which is an analog waveform, into a digital bitstream. In an example embodiment, quadrature reconstruction circuitry 22 may comprise a translinear circuit and reconstructs the total signal using the root of the sum of the squares of the I and Q signal components. In this manner, synchronous demodulation is kept synchronous.

The nonlinear mixing process not only translates frequencies by the reference carrier, but also scales the reference carrier by the cosine of the phase difference between the transmitted signal and a reference carrier. Because the transmitter and the receiver are at different physical locations, at least some phase asynchrony may exist. In a worst case, a 90 degree phase shift can results in a signal null such that the transmit signal is not received, regardless of transmit signal strength.

In operation, it is more likely that the frequency mismatch results in some degree of phase rotation less than 90 degrees, causing a beat frequency that undermines digital slicing of the transmit signal. In effect, parallel chopper-stabilized signal paths, presented by amplifier 20, and quadrature reconstruction circuitry 22 apply trigonometric identities to reconstruct the net waveform independent of the clock phasing. The parallel signal paths have reference clocks with a 90 degree phase shift, providing a "sine" and a "cosine" scaling, so that the transmit signal can be reconstructed using the root of the sum of the squares, which extracts the net hypotenuse.

Chopper mixer telemetry circuit 16 and, particularly, chopper-stabilized mixer amplifier 20, may provide certain advantages. For example, as previously described, mixer amplifier 20 may provide substantially linear output over a large range of signal levels while operating at low frequency and power. This is a result of the basic architecture of mixer amplifier 20. As another advantage, on-chip, poly-poly capacitors may be used to implement capacitors in feedback loop 24. Poly-poly capacitors enable fast switching dynamics and can be formed on-chip with other amplifier components. A poly-poly capacitor may be formed on chip with other devices by combining two polysilicon electrodes and an intervening silicon dioxide dielectric. In addition, the gain of mixer amplifier 20 can be set by the ratio of capacitors in feedback loop 24 to capacitors at the input of receiver 14 and centered around a selected reference voltage. Further, by modulating the input signal at transmitter 12, the common mode input voltage can swing from rail to rail and mixer amplifier 14 is still able to extract a differential voltage. These advantages are merely exemplary of those that may be provided in some embodiments of a chopper mixer telemetry circuit. Additional advantages are discussed in this disclosure or may occur to those skilled in the art upon consideration of this disclosure. Moreover, such advantages may not coexist in every embodiment.

Figure 2:
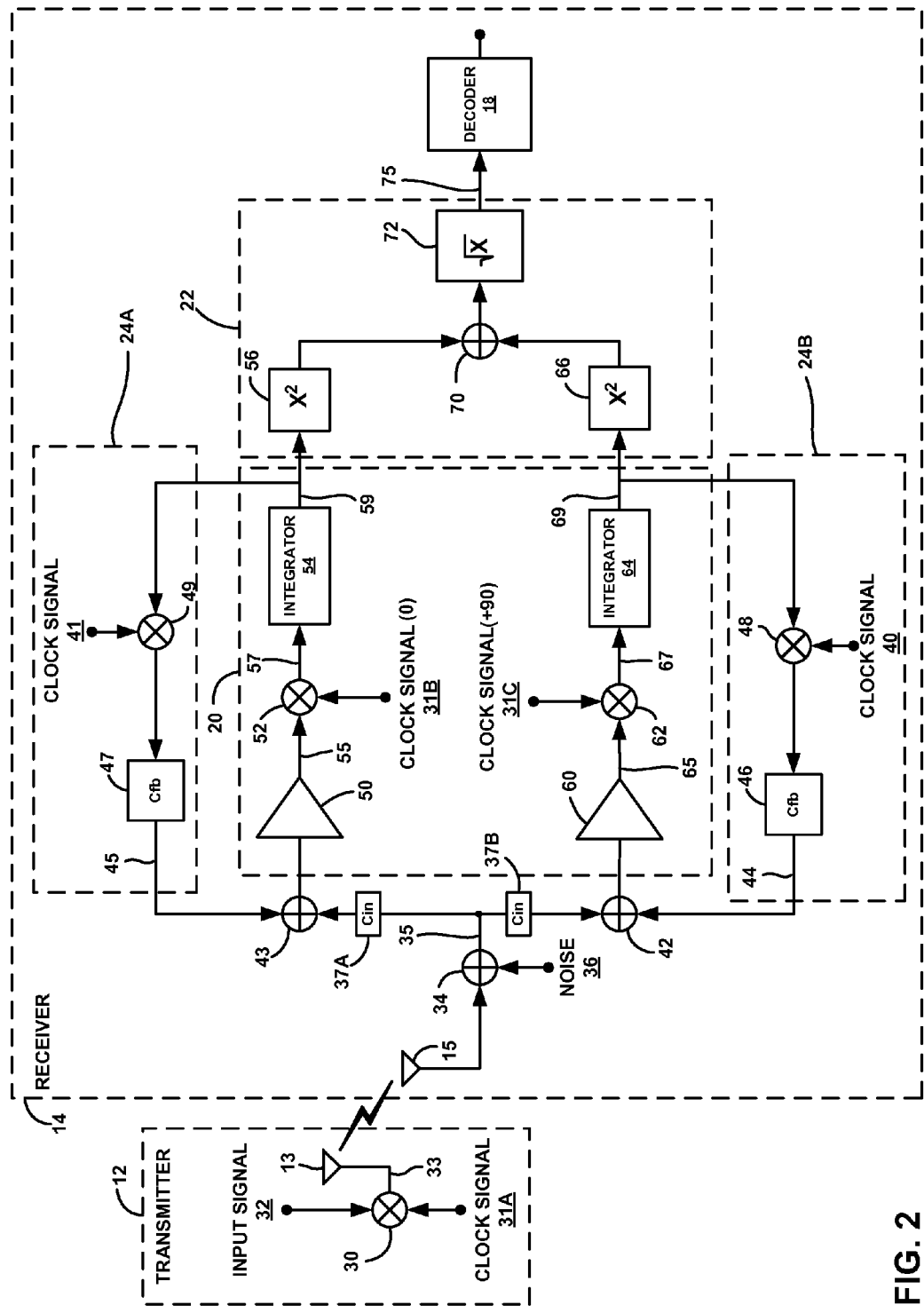
FIG. 2 is a diagram illustrating a signal flow path for the system of FIG. 1.

FIG. 2 is a block diagram illustrating a signal path flow for system 10 which incorporates linear micropower mixer amplifier 20 in receiver 14. As previously described, system 10 includes transmitter 12 and receiver 14, which may be configured to support ALT. In one example embodiment, transmitter 12 may be located in an external programmer and receiver 14 may be located in an IMD in communication with transmitter 12. In another example embodiment, transmitter 12 may be located in an IMD and receiver 14 may be located in an external programmer in communication with the IMD. Alternatively, one of transmitter 12 and receiver 14 may be located in a different IMD or a different external medical device.

The signal flow depicted in FIG. 2 begins with transmitter 12, which includes modulator 30. Modulator 30 receives an input data signal 32 and chops (modulates) the input signal at a chopping (carrier) frequency defined by clock signal 31A to produce an output signal 33 for RF transmission to receiver 14. Clock signal 31A, like other clock signals described in this disclosure, may be a square wave signal that effectively multiples the signal by plus 1 and minus 1 at a desired clock frequency. Modulator 30 may, in some embodiments, comprise a pair of complementary metal oxide semiconductor (CMOS) single pole, double throw (SPDT) switches that are driven by clock signal 31A to modulate (chop) input signal 32 to the RF carrier frequency. The CMOS SPDT switches may be cross-coupled to each other to reject common mode signals.

Additional amplifier or filter components may be provided to generate data signal 32. Generally, input data signal 32 is an electrical signal encoded with data. More specifically, transmitter 12 may convert a digital bit stream into an analog waveform represented by data signal 32. Data input signal 32 may be encoded, for example, using on-off-keying and modulated to 175 kHz for transmission over a wireless channel via transmit antenna 13. The data may be framed with a fixed interval of 228 µs to provide a 4.4 kbps data rate. The duty cycle of signal 33 within the frame signifies whether the data bit is a zero or a one. In this way, transmitter 12 produces telemetry signal 33 for transmission over a wireless channel via transmit antenna 13. The wireless channel, in this case, is the path that telemetry signal 33 travels from transmitter 12 to receiver 14.

Telemetry signal 33 is received by receiver 14 via receive antenna 15. Antenna 15 of the wireless channel may be realized, in some embodiments, by a resonant circuit having a tuned center frequency $f_0$ and resonant quality factor Q. Summing node 34 represents the introduction of noise 36 into telemetry signal 33 to produce noisy modulated input signal 35. Noise 36 includes out-of-band aggressors that are introduced by the environment and noise introduced by amplifier 20. Example out of band aggressors include parasitic magnetic fields induced by stimulation currents in the IMD, cathode ray tubes, and other similar electromagnetic phenomena. Noise introduced by amplifier 20 includes low frequency 1/f noise, popcorn noise, and offset. At node 34, however, the desired data has already been chopped (modulated) to a higher frequency band (carrier frequency) by modulator 30 of transmitter 12. Thus, the low frequency noise 36 is segregated from the modulated data at the input of mixer amplifier 20.

For antenna 16, when tuned to the telemetry frequency with significantly high Q factor, out of band aggressors having significant transient components can generate aggressor signals at the tuned frequency. These aggressors may then be mixed down to the baseband causing interference to the desired telemety signal. In some embodiments, to take advantage of the aggressor rejection of the mixing process, an antenna 15 of moderate Q may be tuned above or below the telemetry frequency by a margin to yield a damped natural response (ringing) at a frequency that will be mixed sufficiently away from the telemetry baseband signal.

Feedback summing nodes 42, 43 will be described below in conjunction with two feedback paths 24A, 24B that collectively form feedback path 24 for the parallel signal paths of chopper mixer telemetry circuitry 16. Mixer amplifier 20 receives noisy modulated input signal 35 from summing nodes 42, 43 via series input capacitors (Cin) 37A, 37B, respectively. In the example of FIG. 2, mixer amplifier 20 includes parallel signal paths that convert noisy modulated input signal 35 into I and Q components. For purposes of description, the upper or top signal pathway converts input signal 35 into the I signal component and the bottom or lower signal pathway converts input signal 35 into the Q signal component. Thus, the upper signal path (I) includes a gain amplifier 50, modulator 52, and integrator 54 that amplify, modulate and integrate a first version of the received telemetry signal, and the lower or bottom signal path (Q) includes a gain amplifier 60, modulator 62, and integrator 64 that amplify, modulate and integrate a second version of the received telemetry signal.

The received signal 35 is applied to inputs of both amplified 50 and amplifier 60. Amplifiers 50 and 60 amplify signal 35 to produce amplified signals 55 and 65, respectively, and may have differential inputs. Modulators 52 and 62 demodulate amplified signals 57 and 67 to baseband to generate demodulated signals 57 and 67, respectively. In this operation, the desired signal components at the carrier frequency are modulated down to baseband and low frequency noise 36 is modulated up to the carrier frequency in demodulated signals 57 and 67. In this manner, the noise can be filtered out of the resulting signal, leaving the desired transmit signal. Modulators 52 and 62 are driven by clock signals 31B and 31C, respectively, and operate at the same frequency as modulator 30 driven by clock signal 31A. However, modulators 52 and 62 are 90 degrees out of phase with each other. In this way, modulators 52 and 62 convert the received telemetry signal into in-phase (I) and quadrature (Q) components 59 and 69, respectively. Modulators 52, 62 may not be synchronized with the phase of modulator 30 of transmitter 12. However, the combination parallel I and Q paths with quadrature reconstruction circuitry 22 permits synchronization.

In some embodiments, clock signals 31B and 31C may be derived from the same clock, such as a clock operating at 700 Hz. In such embodiments, additional circuitry may be provided to downsample the output of this clock to obtain a good (stable) duty cycle and phase at 350 Hz. Then, this downsampled clock signal can be sampled again to produce acceptable 175 kHz signals that can be used for clock signals 31B and 31C.

Demodulated signals 57 and 67 are received by integrators 54 and 64, respectively. Integrators 54 and 64 suppress components in the demodulated signals that are not at baseband, thereby producing output signals 59 and 69, respectively, that are substantially free of noise 36. In other words, integrators 54, 64 serve to remove the high frequency noise components that were chopped up to the modulation frequency, and retain the low frequency signal components that were chopped down to the baseband frequency. Output signals 59 and 69 are also referred to in this disclosure as the I and Q signal components. Integrators 54 and 64 provide compensation and filtering. In other embodiments, compensation and filtering may be provided by other circuitry. However, the use of integrators 54 and 64 as described in this disclosure may be desirable. FIG. 4 provides a detailed circuit diagram of an example embodiment of the a signal path for use as one of the parallel signal paths of mixer amplifier 20.

Quadrature reconstruction circuitry 22 reconstructs the total received signal using I and Q components or output signals 59 and 69. In an example embodiment, quadrature reconstruction circuitry may be implemented using a translinear circuit. In FIG. 2, quadrature reconstruction circuitry 22 includes squaring units 56 and 66, summing unit 70, and root unit 72. Squaring unit 56 squares the output of integrator 54. Squaring unit 56 squares the output of integrator 64. Summing unit 70 adds the squared outputs of integrators 54 and 64 to produce a summed signal. Root unit 72 produces a square root of the summed signal.

Figure 3:
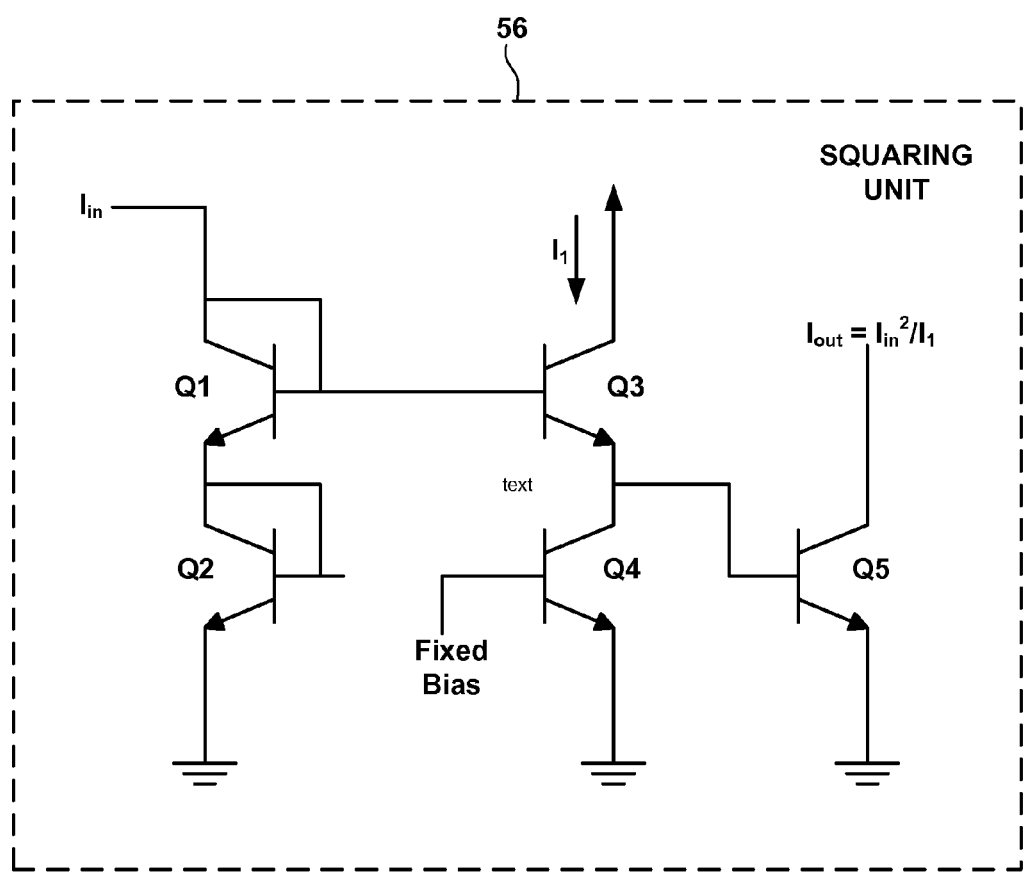
FIG. 3 is a circuit diagram illustrating an example squaring unit for use in the system of FIG. 1.

The total signal can be reconstructed using the root of the sum of the squares of the I and Q components. In other words, using a "sine" and "cosine" scaling of the received signal, the net hypotenuse of the total signal is extracted independent of phase mismatch between transmitter 12 and receiver 14. In this manner, phase synchronization can be achieved relative to transmitter 12. Each squaring unit 56, 66 may be formed in a variety of ways, e.g., using any of a variety of translinear circuits known to those skilled in the art. FIG. 3, discussed below, illustrates one example squaring unit circuit for squaring units 56, 66. In some embodiments, square root unit 72 may not be necessary as the level for triggering the demodulator data could be based on the squared signal, which contains both the vector inputs of the received signal. Accordingly, square root unit 72 may be optional. If included, square root unit 72 may be formed using any of a variety of translinear circuits known to those skilled in the art, e.g., such as circuits similar to that shown in FIG. 3 for squaring unit 56.

It should be understood that other quadrature reconstruction techniques are possible and may be implemented using circuitry other than that illustrated in FIG. 2. Accordingly, FIG. 2 describes an example for reconstructing the total signal using quadrature components, but it is recognized that those skilled in the art may apply other reconstruction techniques and circuits for implementing these techniques.

The output of quadrature reconstruction circuitry 22 is reconstructed signal 75 which is passed to decoder 18. Decoder 18 produces a digital bitstream 77 from signal 75 by, for example, comparing the amplitude of signal 75 to a threshold value. When the signal exceeds the threshold value, the output bit may be determined to be a 1. When the signal does not exceed the threshold value, the output bit may be determined to be a 0.

In FIG. 2, feedback loop 24 includes an upper or top feedback path 24A and a lower or bottom feedback path 24B. These feedback paths 24A, 24B provide negative feedback to the input of mixer amplifier 20 and, more particularly, to gain amplifiers 50 and 60, respectively, to reduce glitching in output signals 59 and 69. In particular, the feedback paths drive noisy modulated input signal 35 toward zero in steady state. In this way, the feedback paths keep the signal change at the input to mixer amplifier 20 small, thereby reducing undesirable glitching. Feedback path 24A applies feedback to the version of the input signal 35 applied to amplifier 50, and feedback path 24B applies feedback to the version of the input signal applied to amplifier 60.

In the example of FIG. 2, the upper feedback path includes modulator 49 and feedback capacitor (Cfb) 47. The lower feedback path includes modulator 48 and feedback capacitor (Cfb) 46. Modulators 49 and 48 modulate output signals 59 and 69, respectively, to produce feedback signals 45 and 44 that are added to the signal path at the input of gain amplifiers 50 and 60 via summing nodes 43 and 42, respectively.

Each of the feedback paths may provide capacitor scaling versus the input capacitance of mixer amplifier 20 to produce attenuation and thereby generate gain at the output of amplifier 20. Accordingly, feedback capacitors 47 and 46 may be selected to produce the desired gain given the value of the input capacitance of mixer amplifier 20.

Clock signals 40, 41 drive modulators 48, 49, respectively, to modulate output signals 69, 59 at the carrier frequency, e.g., 175 kHz. Clock signals 40, 41 may be derived from the same clock as clock signals 31B, 31C. More specifically, clock signal 40 may be synchronized with clock signal 31C and clock signal 41 may be synchronized with clock signal 31B. Thus, clock signals 40, 41 may be approximately 90 degrees out of phase with each other.

However, because output signals 59 and 69 of the upper and lower feedback paths are single ended, upper and lower feedback paths may each include two feedback paths that apply negative feedback to the positive and negative input terminals of gain amplifiers 50 and 60, respectively, which may be differential amplifiers. A single feedback path is shown for the upper and lower feedback paths in FIG. 2 in the interest of simplicity.

The two feedback paths, referred to as differential feedback paths, for each of the upper and lower feedback paths should be approximately 180 degrees out of phase with each other. One of the differential feedback paths for each of the upper and lower feedback paths should modulate synchronously with modulators 52 and 62, respectively. This ensures that a negative feedback path exists during each half of the clock cycle.

As an alternative, in some embodiments, mixer amplifier 20 may be configured such that each of the parallel signal paths generates a differential output signal, rather than a single-ended output signal. A differential output signal may provide positive and negative outputs. In this case, the upper and lower feedback paths can apply negative feedback to the positive inputs of gain amplifiers 50 and 60, respectively, and apply negative feedback to the negative inputs of gain amplifiers 50 and 60. For a differential output signal, the upper and lower feedback paths would modulate each of the positive and negative output signals. However, the positive and negative output signals could be modulated in-phase, rather than out of phase. Although differential output signals are possible, a feedback path configured to convert a single-ended output to differential feedback will be described herein for purposes of illustration.

FIG. 3 is a circuit diagram illustrating an example squaring unit for use in the system of FIG. 1. FIG. 3 illustrates squaring unit 56 for processing an I component produced by integrator 54 (FIG. 2). In the example of FIG. 3, squaring unit 56 includes NPN bipolar transistors Q1, Q2, Q3, Q4, Q5. The emitter of transistor Q1 receives the output of integrator 54, which is labeled $I_{in}$ in FIG. 3 to designate an electrical current value associated with the signal produced by integrator 54. Squaring unit 66, which processes the output of integrator 64, may be identical to squaring unit 56. With further reference to FIG. 3, the base and emitter of transistor Q1 are coupled to one another and to the base of transistor Q3. The emitter and base of transistor Q2 are coupled to the collector of transistor Q1. The collector of transistor Q2 is coupled to ground. Transistor Q3 receives an electrical current $I_1$ via the emitter and has a collector coupled to the emitter of transistor Q4 and the base of transistor Q5. The base of transistor Q4 is coupled to a fixed bias potential, and the collector of transistor Q4 is coupled to ground. The collector of transistor Q5 is coupled to ground. The emitter of transistor Q5 produces the squared output current value $I_{out}=I_{in}^2/I_1$, which then can be applied to summer 70 and square root unit 72 with the corresponding output of squaring unit 66.

FIG. 4 is a circuit diagram illustrating an example embodiment of mixer amplifier 20 in greater detail. More specifically, FIG. 4 is a circuit diagram illustrating one of the signal paths of mixer amplifier 20, such as the upper signal path or lower signal path. Both signal paths are not illustrated in the interest of simplicity. Thus, with respect to FIG. 2, the circuit diagram in FIG. 4 can be viewed as a circuit diagram for gain amplifier 50, modulator 52, and integrator 54.

In the example of FIG. 4, the upper signal path of mixer amplifier 20 is a modified folded-cascode amplifier with switching at low impedance nodes. The modified folded-cascode architecture allows the currents to be partitioned to maximize noise efficiency. In general, the folded cascode architecture is modified in FIG. 4 by adding two sets of switches. One set of switches is illustrated in FIG. 4 as switches 80A and 80B (collectively referred to as "switches 80") and the other set of switches includes switches 82A and 82B (collectively referred to as "switches 82").

Switches 80 are driven by chop logic to support the chopping of the amplified signal for demodulation at the chop clock frequency. In particular, switches 80 demodulate the amplified signal down to baseband and modulate front-end offsets and 1/f noise up to the clock frequency. Switches 82 are embedded within a self-biased cascode mirror formed by transistors M6, M7, M8 and M9, and are driven by chop logic to up-modulate the low frequency errors from transistors M8 and M9. Low frequency errors in transistors M6 and M7 are attenuated by source degeneration from transistors M8 and M9. The demodulated signal is at baseband, allowing an integrator 54, formed by transistor M10 and capacitor 83 (Ccomp), to stabilize the upper feedback path (not shown in FIG. 4) and filter modulated offsets.

The upper signal path of mixer amplifier 20 and, thus, the circuit diagram in FIG. 4 has three main blocks: a transconductor, a demodulator, and an integrator. The core is similar to a folded cascode. In the transconductor section, transistor M5 is a current source for the differential pair of input transistors M1 and M2. In an example embodiment, transistor M5 may pass approximately 800 nA, which is split between transistors M1 and M2, e.g., 400 nA each. Transistors M1 and M2 are the inputs to gain amplifier 50. Small voltage differences steer differential current into the drains of transistors M1 and M2 in a typical differential pair way. Transistors M3 and M4 serve as low side current sinks, and may each sink roughly 500 nA, which is a fixed, generally nonvarying current. Transistors M1, M2, M3, M4 and M5 together form a differential transconductor.

In this example, approximately 100 nA of current is pulled through each leg of the demodulator section. The alternating current (AC) current at the chop frequency from transistors M1 and M2 also flows through the legs of the demodulator. Switches 80 alternate the current back and forth between the legs of the demodulator to demodulate the measurement signal back to baseband, while the offsets from the transconductor are up-modulated to the chopper frequency. As discussed previously, transistors M6, M7, M8 and M9 form a self-biased cascode mirror, and make the signal single-ended before passing into the output integrator formed by transistor M10 and capacitor 83 (Ccomp). Switches 82 placed within the cascode (M6-M9) upmodulate the low frequency errors from transistors M8 and M9, while the low frequency errors of transistor M6 and transistor M7 are suppressed by the source degeneration they see from transistors M8 and M9. Source degeneration also keeps errors from Bias N2 transistors 86 suppressed. Bias N2 transistors M12 and M13 form a common gate amplifier that presents a low impedance to the chopper switching and passes the signal current to transistors M6 and M7 with immunity to the voltage on the drains.

The output direct current (DC) signal current and the upmodulated error current pass to the integrator, which is formed by transistor M10, capacitor 83 (Ccomp), and the bottom NFET current source transistor M11. Again, this integrator serves to both stabilize the upper feedback path and filter out the upmodulated error sources. The bias for transistor M10 may be approximately 100 nA in an example embodiment, and is scaled compared to transistor M8. The bias for lowside NFET M11 may also be approximately 100 nA (sink). As a result, the integrator is balanced with no signal. If more current drive is desired, current in the integration tail can be increased appropriately using standard integrate circuit design techniques. Various transistors in the example of FIG. 4 may be field effect transistors (FETs), and more particularly CMOS transistors. The output of the circuit in FIG. 4 is output signal or I component 59, which is passed to quadrature reconstruction circuitry 22. The lower signal path of mixer amplifier 20 may be implemented using a circuit similar to the circuit depicted in FIG. 4.

Figure 5:
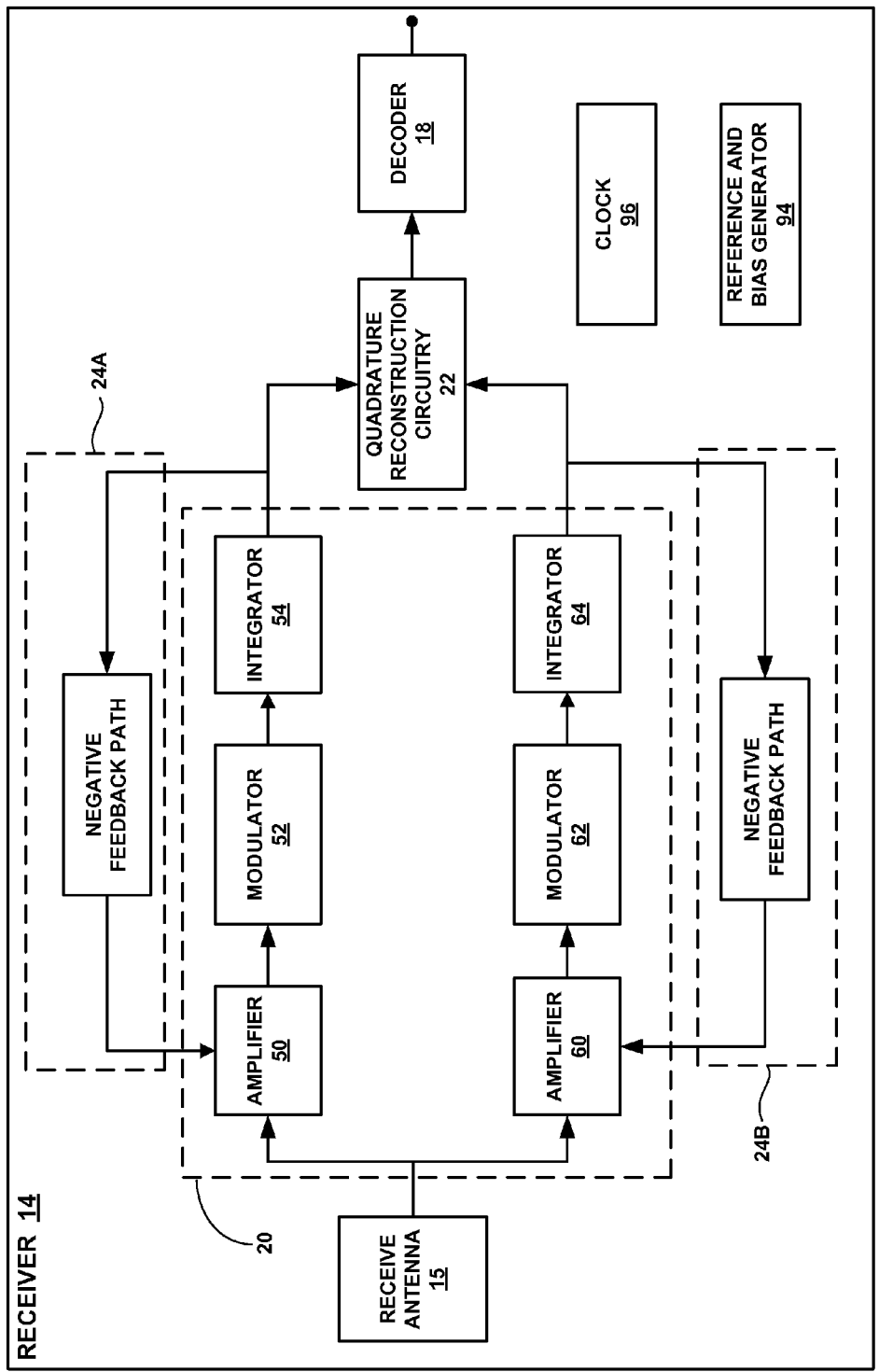
FIG. 5 is a block diagram illustrating an example embodiment of the receiver of FIG. 1.

FIG. 5 is a block diagram illustrating receiver 14. It should be understood that FIG. 5 is merely exemplary and should not be considered limiting. FIG. 5 illustrates the operation of receiver 14. In FIG. 5, receive antenna 15 receives the telemetry signal, i.e., telemetry signal 33, generated by transmitter 12 (not shown) that carries the data encoded output signal at a carrier frequency over a wireless channel. Noise, e.g., l/f noise, popcorn noise, and offset, enters the signal path of mixer amplifier 20 to produce the noisy modulated input signal at the input to mixer amplifier 20. The noise may also include out-of-band aggressors, such as parasitic magnetic fields induced by stimulation currents in the IMD, cathode ray tubes, and other similar phenomena. In addition, some of the noise may be produced within mixer amplifiers 50, 60, e.g., as l/f noise, offset, or popcorn noise. Thus, the signal processed by mixer amplifier 20 includes the data modulated up to the carrier frequency and noise components at baseband.

As previously described, mixer amplifier 20 may be implemented using parallel signal paths that convert the received noisy signal into I and Q components. The parallel signal paths may be implemented using the modified folded-cascode amplifier architecture illustrated in FIG. 4 for each signal path. Mixer amplifier 20 is illustrated in FIG. 5 as including amplifiers 50 and 60, demodulators 52 and 62, and integrators 54 and 64, forming respective parallel I and Q chopper mixer paths.

Quadrature reconstruction circuitry 84 combines the output of mixer amplifier 20, i.e., I and Q components 59 and 69, to reconstruct the received signal. As previously described, in an example embodiment, quadrature reconstruction circuitry 22 includes circuitry for reconstructing the signal using the root of the sum of the squares of the I and Q components. The circuitry may be implemented using a translinear circuit and include components that correspond to the components depicted in FIG. 2.

Decoder 18 produces a digital bitstream based on the output of quadrature reconstruction circuitry 22. For example, decoder 18 may include a slicer formed from a comparator that detects a level of the output signal produced by quadrature circuitry 22. The comparator may have a dynamic level adjustment to account for variations in the background noise floor. Mild hysteresis may be added to the slicer to prevent multiple triggers in the digital waveform for small amplitude transitions over short periods of time.

In FIG. 5, feedback path 24 includes an upper negative feedback path 24A and lower negative feedback path 24B. To provide a differential-to-single ended conversion, each of feedback paths 24A and 24B may include two symmetrical feedback path branches, referred to as differential feedback path branches, to provide feedback to respective positive and negative differential inputs of mixer amplifier 20, i.e., positive and negative inputs of amplifiers 50 and 60.

Negative feedback paths 24A and 24B apply negative feedback to keep the signal change small at the input to mixer amplifier 20, and thereby reduce glitching. Each of the differential feedback path branches of negative feedback paths 24A and 24B modulates the corresponding output signal of mixer amplifier 20, i.e., output signals 59 and 69, with a reference voltage provided by reference and bias generator 94. To ensure that a negative feedback path exists in negative feedback paths 24A and 24B at all times, the chop frequency applied to the differential branches of negative feedback paths 24A and 24B should be 180 degrees out of phase with each other. Additionally, one of the differential feedback path branches for each of negative feedback paths 24A and 24B should be synchronized with the modulator in the corresponding signal path.

For example, with respect to FIG. 5, one of the differential branches of negative feedback path 24A should be synchronized with modulator 52 and one of the differential branches of negative feedback path 24B should be synchronized with modulator 62. In this way, one of the differential branches of negative feedback paths 24A and 24B is applying negative feedback during each half of the clock cycle. As a result, the differential signals at the input of mixer amplifier 20 are small and centered about the reference voltage. Negative feedback paths 24A and 24B substantially reduce or eliminate the dynamic limitations of mixer amplifier 20, i.e., glitching in the output signals produced by integrators 54 and 64 (output signals 59 and 69 with respect to FIG. 2).

In some embodiments, clock 96 may comprise one or more clocks. In one example embodiment, clock 96 may be a single clock and includes circuitry for deriving the clock signals for mixer amplifier 20 and feedback paths 24A and 24B. In an example embodiment in which transmitter 12 modulates the input signal to 175 kHz, clock 96 may be a clock operating at approximately 700 kHz and additional circuitry may be used to down sample the 700 kHz clock to obtain the required clock signals. The additional circuitry may, for example, sample the output of the clock to obtain a stable duty cycle and phase at 350 kHz. From these signals, the 175 kHz clock signals required for mixer amplifier 20 and feedback paths 90 and 92 can be obtained. Hence, the 700 kHz signal may be downsampled to 350 kHz, and then to 175 kHz for application to modulators 52, 62, and application within negative feedback paths 24A, 24B.

Reference and bias generator 94 supplies bias voltages to mixer amplifier 20 and negative feedback paths 24A and 24B. With respect to mixer amplifier 20, reference and bias generator 94 may supply bias voltages for biasing the transistors as shown in FIG. 4. Reference and bias generator 94 may also supply the reference voltages that are mixed with the signals in negative feedback paths 24A and 24B. Bias voltages of 0 volts to 1.2 volts (bandgap) or 0 volts to 0.6 volts (half bandgap) may be used as bias points.

Figure 6:
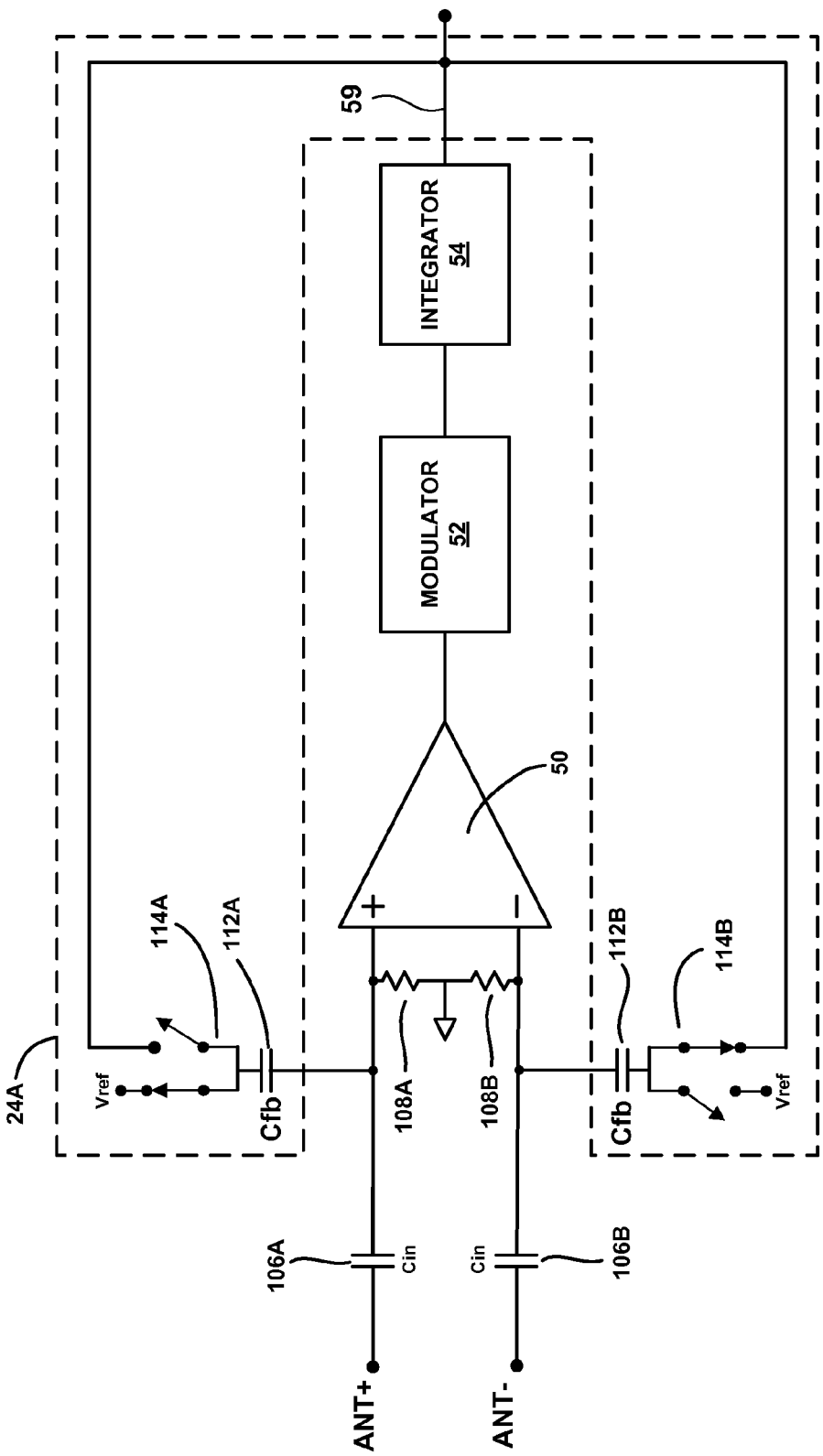
FIG. 6 is a circuit diagram illustrating an example embodiment of a chopper-stabilized mixer amplifier as shown in FIG. 1 in greater detail.

FIG. 6 is a circuit diagram illustrating an example embodiment of one signal path of chopper mixer telemetry circuit 16 of receiver 14. In particular, the circuit diagram in FIG. 6 depicts input and feedback circuitry for a portion of chopper mixer telemetry circuit 16 of receiver 14. The portion depicted in FIG. 6 includes the upper signal path of mixer amplifier 20 and positive and negative differential branches of negative feedback path 24A. The lower signal path of mixer amplifier 20, quadrature circuitry 22, and decoder 18 are not illustrated in the interest of simplicity. However, those skilled in the art will recognize that the lower signal path of receiver 14 may also generally conform to the circuit diagram in FIG. 6.

As shown in FIG. 6, gain amplifier 50 receives telemetry signal 33, i.e., a modulated differential input signal, via input capacitors (Cin) 106A, 106B. Input capacitors 106A, 106B may correspond to input capacitor 37A of FIG. 2. Input capacitor 106A feeds a positive end of the differential antenna signal (ANT+) to the positive input of gain amplifier 50. Input capacitor 106B feeds a negative end of the differential antenna signal (ANT−) to the negative input of gain amplifier 50.

Resistors 108A, 108B (collectively referred to as "resistors 108") may be provided to set the inputs of mixer amplifier 14 to set an input bias impedance. That is, resistors 108 provide a DC conduction path that controls the voltage bias at the input of gain amplifier 50. Thus, resistors 108 are selected to provide an equivalent resistance that is used to keep the bias impedance high. Resistors 108 may, for example, be selected to provide approximately a 5 GΩ equivalent resistor, but the absolute size of the equivalent resistor is not critical to the performance of gain amplifier 50. In general, increasing the impedance improves the noise performance and rejection of harmonics, but extends the recovery time from an overload. To provide a frame of reference, a 5 GΩ equivalent resistor results in a referred-to-input (RTI) noise of approximately 20 nV/rt Hz with an input capacitance, provided by input capacitors 106A, 106B, of approximately 25 pF. Therefore, one reason for keeping the impedance high is the rejection of high frequency harmonics which can alias into the signal chain due to settling at the input nodes of gain amplifier 50 during each half of a clock cycle.

It is important to note that resistors 108 are merely exemplary and serve to illustrate one of many different biasing schemes for controlling the signal input to gain amplifier 50. In fact, the biasing scheme is flexible because the absolute value of the resulting equivalent resistance is not critical. In general, the time constant of resistors 108 and input capacitors 106A, 106B may be selected to be approximately 100 times longer than the reciprocal of the chopping (carrier) frequency.

As previously described, operating at low power tends to limit the bandwidth of gain amplifier 50 and creates distortion (ripple or glitching) in the output signal, i.e., output signal 59. The upper signal path of mixer amplifier 20 and feedback path 24A operate as previously described. That is, gain amplifier 50, modulator 52, integrator 54 and feedback path 24A may provide a substantially linear output over a large change in signal level, e.g., from hundreds of millivolts to hundreds of microvolts, while substantially eliminating the dynamic limitations of chopper stabilization through a combination of chopping at low-impedance nodes and AC feedback. Consequently, mixer amplifier 20 can provide synchronous demodulation and substantially reduce or eliminate out of band aggressors in the output signal 59. As a result, mixer amplifier 20 outputs a signal that is an amplified representation of received telemetry signal.

Without the negative feedback provided by feedback path 24A, output signal 59 could include spikes superimposed on the desired signal because of the limited bandwidth of the amplifier at low power. However, the negative feedback provided by feedback path 24A can suppress these spikes so that the output signal in steady state is an amplified representation of the received telemetry signal with very little noise.

Feedback path 24A in FIG. 6 includes two feedback paths, i.e., differential branches of feedback path 24A, that provide a differential-to-single ended interface. The top branch modulates output signal 59 to provide negative feedback to the positive input terminal of gain amplifier 50. This branch includes capacitor 112A and switch 114A. Similarly, the bottom branch of feedback path 24A includes capacitor 112B and switch 114B that modulate output signal 59 to provide negative feedback to the negative input terminal of gain amplifier 50. Capacitors (Cfb) 112A and 112B are connected at one end to switches 114A and 114B, and at the other end to the positive and negative input terminals of mixer amplifier 20, respectively. With respect to FIG. 2, capacitors 112A and 112B correspond to capacitor 47.

Switches 114A and 114B toggle between a reference voltage (Vref), which may be provided by reference and bias voltage generator 94 shown in FIG. 5, and output signal 59 to place a charge on capacitors 112A and 112B, respectively. The reference voltage may be, for example, a mid-rail voltage between a maximum rail voltage of amplifier 20 and ground. For example, if the amplifier circuit is powered with a source of 0 to 2 volts, then the mid-rail Vref voltage may be on the order of 1 volt. Importantly, switches 114A and 114B should be approximately 180 degrees out of phase with each other to ensure that a negative feedback path exists during each half of the clock cycle. One of switches 114 should also be synchronized with modulator 52 so that the negative feedback suppresses the amplitude of the input signal to gain amplifier 50 to keep the signal change small in steady state. By keeping the signal change small and switching at low impedance nodes of mixer amplifier 20, e.g., as shown in the circuit diagram of FIG. 4, the only significant voltage transitions may occur at switching nodes. Consequently, glitching (ripples) is substantially eliminated or reduced in output signal 59.

Switches 114, as well as the switches at low impedance nodes of mixer amplifier 20, may be CMOS single pull double throw (SPDT) switches. CMOS switches provide fast switching dynamics that enables switching to be viewed as a continuous process. The transfer function of the upper signal path of mixer amplifier 20, and similarly for the lower signal path, may be defined by the transfer function provided in equation (1) below, where Vout is the voltage of output signal 59, Cin is the capacitance of input capacitors 106, ΔVin is the differential voltage at the inputs to gain amplifier 50, Cfb is the capacitance of feedback capacitors 112, and Vref is the reference voltage that switches 114 mix with the output of mixer amplifier 20.

$$Vout = Cin(\Delta Vin)/Cfb + Vref \quad (1)$$

From equation (1), the gain of instrumentation amplifier 20 is set by the ratio of input capacitors Cin and feedback capacitors Cfb, i.e., capacitors 106 and capacitors 112 with respect to FIG. 6. The ratio of Cin/Cfb may be selected to be on the order of 100. Capacitors 112 may be poly-poly, on-chip capacitors or other types of MOS capacitors and should be well matched, i.e., symmetrical.

As shown in FIGS. 4 and 5, chopper telemetry circuit 20 may include an I path having first mixer amplifier 50 that amplifies a telemetry signal modulated at a clock frequency to produce a first amplified signal, a modulator 52 that demodulates the first amplified signal at the clock frequency to produce a first demodulated signal, and an integrator 54 that extracts a portion of the first demodulated signal to produce a first output signal. In addition, chopper telemetry circuit 20 may include a Q path having second mixer amplifier 60 that amplifies the telemetry signal to produce a second amplified signal, a modulator 62 that demodulates the second amplified signal at the clock frequency to produce a second demodulated signal that is approximately 90 degrees out of phase with the first demodulated signal, and an integrator 64 that extracts a portion of the second demodulated signal to produce a second output signal.

A first modulator 52 modulates an amplitude of the first output signal at the clock frequency, and a second modulator 62 modulates an amplitude of the second output signal at the clock frequency. A first feedback path 24A applies the first modulated output signal as a first feedback signal to the first mixer amplifier 50. A second feedback path 24B applies the second modulated output signal as a second feedback signal to the second mixer amplifier 60. Quadrature reconstruction circuitry 22 combines the first and second output signals to produce a third output signal.

Figure 7:
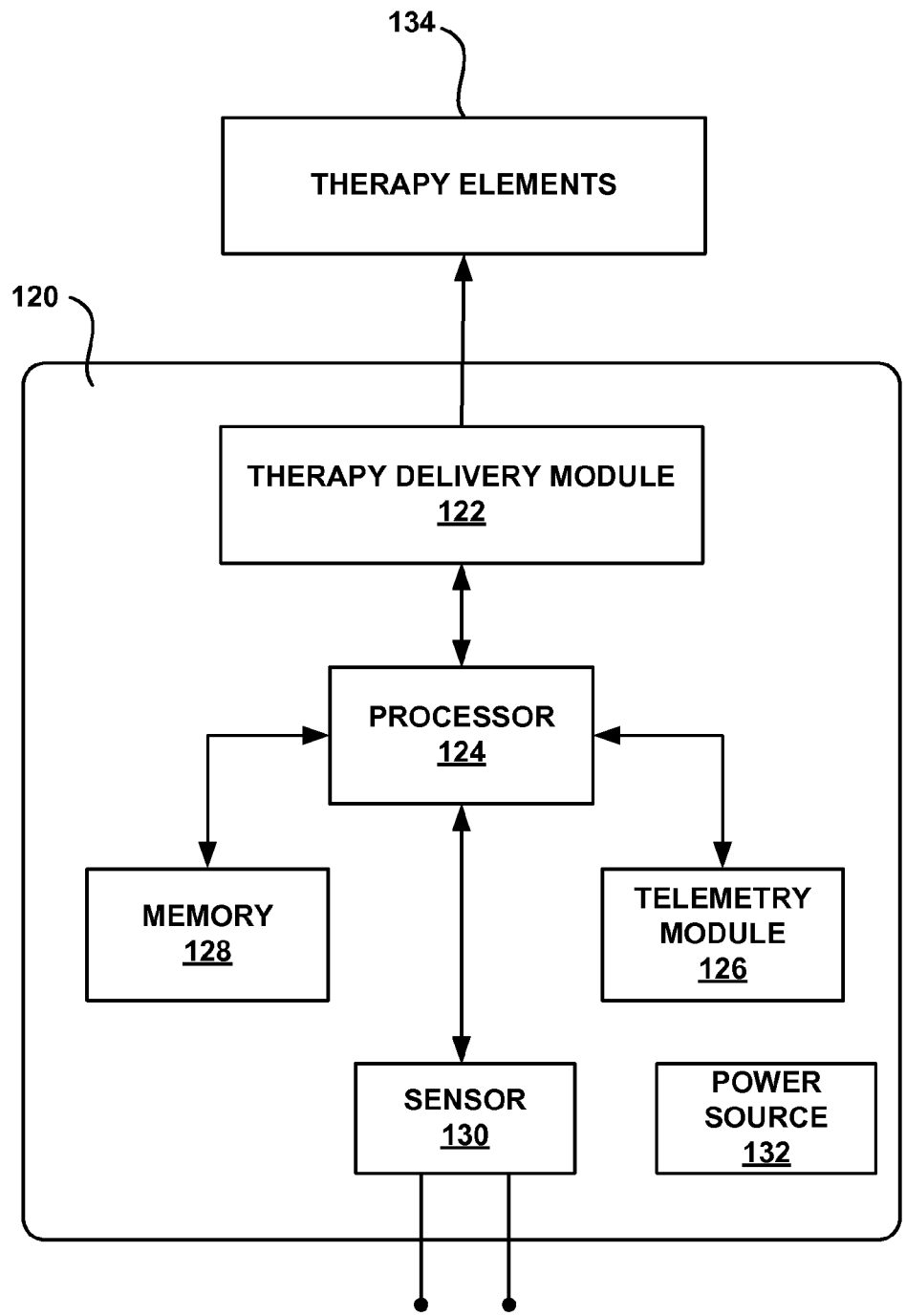
FIG. 7 is a block diagram illustrating an IMD having a telemetry module that includes a receiver as shown in FIG. 1.

As shown in FIG. 6, each mixer amplifier 50, 60 may have first and second differential inputs. The first feedback path 24A includes a first feedback path branch coupled to the first input of the first mixer amplifier and a second feedback path branch coupled to the second input of the first mixer amplifier. Similarly, the second feedback path includes a third feedback path branch coupled to the first input of the second mixer amplifier and a fourth feedback path branch coupled to the second input of the second mixer amplifier. First modulator 52 may include a modulator in the first feedback path branch, e.g., formed by switch 114A, and a modulator in the second feedback path branch, e.g., formed by switch 114B that modulate the amplitude of the first output signal out of phase with each other. Second modulator 62 may include similar first and second modulators in the third feedback path branch and fourth feedback path branch, respectively. Each feedback path branch may include a feedback capacitance (Cfb). The inputs of mixer amplifiers 50, 60 may receive the telemetry signal via an input capacitance (Cin). As a result, the gain of each mixer amplifier 50, 60 may be at least partially dependent on a ratio of the first feedback capacitance to the first input capacitance FIG. 7 is a block diagram illustrating various components of an implantable medical device (IMD) 120 including a receiver that may incorporate a chopper mixer telemetry circuit as described in this disclosure. Accordingly, IMD 120 may be configured to communicate via ALT with an external programmer, another IMD, or another external medical device. In the example of FIG. 1, IMD 120 includes therapy delivery module 122, processor 124, memory 128, telemetry module 126, sensor 130, power source 132, and therapy elements 134. In general, IMD 120 includes a chopper mixer telemetry circuit as part of telemetry module 126.

IMD 120 may be dedicated to therapy, such as delivery of electrical stimulation or drug delivery. Alternatively, IMD 120 may be dedicated to sensing or a combination of therapy and sensing. In embodiments in which IMD 120 includes a sensor 130, the sensor may include any type of sensor or combination of sensors. For example, sensor 130 may be a pressure sensor, accelerometer, activity sensor, impedance sensor, electrical signal sensor or other sensor configured to monitor heart sounds, brain signals, and/or other physiological signals. Although illustrated in FIG. 7 as contained within IMD 120, a portion of sensor 130 may be located outside of IMD 120. For example, a sensor transducer or one or more electrodes may be located on a distal tip of a lead implanted at a target site within the patient and electrically coupled to IMD 120 via conductors. Alternatively, a sensor transducer or one or more electrodes may be provided on or within a housing of IMD 120. For example, an accelerometer may be provided within an IMD housing or within a lead that extends from the IMD. To sense electrical signals, sensor 130 may include two or more electrodes arranged on a lead, an electrode on a lead and an electrode on an IMD housing, two or more electrodes arranged on an IMD housing, or other electrode arrangements. Sensor circuitry associated with sensor 130 may be provided within sensor 130 in the housing of IMD 120.

In general, sensor 130 provides a measurement of a physiological signal or parameter by translating signal or parameter to an output voltage or current. The output of sensor 130 may be received by processor 124. Processor 124 may apply additional processing, e.g., convert the output to digital values for processing, prior to storing the values in memory 128, and/or transmitting the values to an external programmer via telemetry module 126. Telemetry module 126 may include a receiver with a chopper mixer telemetry circuit as described in this disclosure. In addition, telemetry module 126 may include a transmitter that transmits data. For example, telemetry module 126 may include receiver 14 which incorporates linear micropower amplifier 20. Processor 124 may also control delivery of therapy to the patient based on the output of sensor 130.

IMD 120 may deliver therapy to a patient via one or more therapy elements 134, which may be within or on, or extend from, a housing associated with IMD 120. In other embodiments, IMD 120 may be dedicated to sensing and may not include therapy delivery module 122. Therapy delivery elements 134 may be electrodes carried on one or more implantable leads, electrodes on the housing of IMD 120, one or more fluid delivery devices, or any combination thereof. For delivery of electrical stimulation, therapy delivery module 122 may include an implantable stimulation generator or other stimulation circuitry that generates electrical signals, e.g., pulses or substantially continuous signals, such as sinusoidal signals, to the patient via at least some of the electrodes that form therapy elements 134 under the control of processor 124.

The stimulation energy generated by therapy delivery module 122 may be formulated as stimulation energy for treatment of any of a variety of cardiac or neurological disorders, or disorders influenced by patient neurological response. Example stimulation therapies include cardiac pacing, cardiac defibrillation, deep brain stimulation (DBS), spinal cord stimulation (SCS), peripheral nerve field stimulation (PNFS), pelvic floor stimulation, gastrointestinal stimulation, muscle stimulation, and the like.

Therapy delivery module 122, processor 124, telemetry module 126, memory 128, and sensor 130 receive operating power from power source 132. Power source 132 may take the form of a small, rechargeable or non-rechargeable battery, or an inductive power interface that transcutaneously receives inductively coupled energy. In the case of a rechargeable battery, power source 132 similarly may include an inductive power interface for transcutaneous transfer of recharge power.

In embodiments in which one or more fluid delivery devices are part of therapy elements 134, therapy delivery module 122 may include a one or more fluid reservoirs and one or more pump units that pump fluid from the fluid reservoirs to the target site through the fluid delivery devices. The fluid reservoirs may contain a drug or mixture of drugs. The fluid reservoirs may provide access for filling, e.g., by percutaneous injection of fluid via a self-sealing injection port. The fluid delivery devices may comprise, for example, catheters that deliver, i.e., infuse or disperse, drugs from the fluid reservoirs to the same or different target sites.

Processor 124 may include a microprocessor, microcontroller, digital signal processor (DSP), application specific integrated circuit (ASIC), field programmable gate array (FPGA), discrete logic circuitry, or a combination of such components. Processor 124 may be programmed to control delivery of therapy according to a selected parameter set stored in memory 128. Specifically, processor 124 controls therapy delivery module 122 to deliver electrical stimulation, drug therapy, or a combination of both. For example, processor 124 may control which drugs are delivered and the dosage of the drugs delivered.

Processor 124 may also control therapy delivery module 122 to deliver electrical stimulation with pulse amplitudes, pulse widths, and frequencies (i.e., pulse rates) specified by the programs of the selected parameter set. Processor 124 may also control therapy delivery module 122 to deliver electrical stimulation or drugs according to a different program of the parameter set. In some embodiments, processor 124 may control therapy delivery module 122 to deliver a substantially continuous stimulation waveform rather than pulsed stimulation.

Memory 128 may store parameter sets that are available to be selected by the patient for delivery of electrical stimulation and/or drug therapy. Memory 128 may also store schedules. Memory 128 may include any combination of volatile, non-volatile, removable, magnetic, optical, or solid state media, such as read-only memory (ROM), random access memory (RAM), electronically-erasable programmable ROM (EEPROM), flash memory, or the like.

Processor 124 may control telemetry module 126 to exchange information with an external programmer, such as a clinician programmer and/or patient programmer, by wireless telemetry. Processor 124 may control telemetry module 126 to communicate with the external programmer on a continuous basis, at periodic intervals, or upon request from the programmer. In addition, in some embodiments, telemetry module 126 may support wireless communication with one or more wireless sensors that sense physiological signals and transmit the signals to IMD 120.

Telemetry module 126 may operate as a transceiver that receives telemetry signals from an external programmer and transmits telemetry signals to an external programmer. A portion of telemetry module 126 is configured operate as a transmitter to transmit signals from IMD 120 to an external programmer or to another IMD or external medical device. The receiver portion of telemetry module 126 may include receiver 14 and, more particularly, linear micropower amplifier 20. Accordingly, telemetry module 126 may support ALT and may communicate with an external programmer at distances of greater than or equal to approximately 5 cm, greater than or equal to approximately 10 cm, greater than or equal to approximately 50 cm, or at distances between approximately 5 cm and approximately 1 meter (m), between approximately 10 cm and approximately 1 m, or between approximately 50 cm and approximately 1 m. ALT may eliminate the burden of placing the external programmer directly over IMD 120 within the patient.

Figure 8:
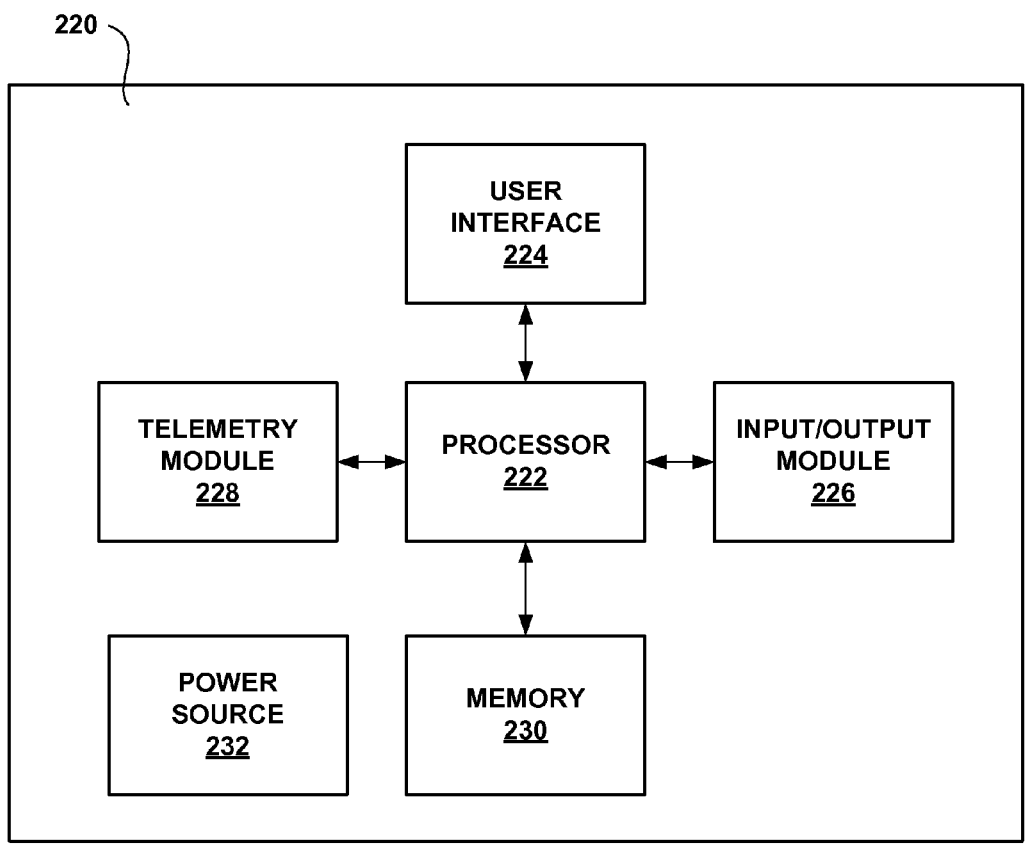
FIG. 8 is a block diagram illustrating a medical device programmer having a telemetry module that includes a receiver as shown in FIG. 1.

FIG. 8 is a block diagram illustrating various components of an example patient or clinician programmer 220 that allows a patient or clinician to communicate with IMD 120. Similar to IMD 120, programmer 220 includes a receiver that incorporates a chopper mixer telemetry circuit, such as that described herein with respect to receiver 14. In general, a patient or clinician may interact with programmer 220 to program or control therapy parameters, e.g., electrical stimulation, drug therapy, or a combination of both. In addition, a programmer may be equipped to interrogate an IMD to retrieve information, such as status, operational, diagnostic or fault information. In the illustrated example, programmer 220 includes processor 222, user interface 224, input/output 226, telemetry module 228, memory 230, and power source 232. Programmer 220 may include a chopper mixer telemetry circuit as part of telemetry module 228.

A patient or clinician, referred to as a user herein, may interact with processor 222 via user interface 224 in order to control delivery of electrical stimulation, drug therapy, or a combination of both. User interface 224 may include a display and a keypad, and may also include a touch screen or peripheral pointing devices as described above. Processor 222 may also provide a graphical user interface (GUI) to facilitate interaction with the user, as will be described in greater detail below. Processor 222 may include a microprocessor, a controller, a DSP, an ASIC, an FPGA, discrete logic circuitry, or the like.

Programmer 220 also includes memory 230. In some embodiments, memory 230 may store parameter sets that are available to be selected by the user for delivery of therapy. Memory 230 may also store schedules. Hence, parameter sets and schedules may be stored in IMD 120, programmer 220, or both. Programmer 220 also includes a telemetry module 228 that allows processor 222 to communicate with IMD 120, and, optionally, input/output circuitry module 226 that allows processor 222 to communicate with another programmer.

Processor 222 may receive parameter set selections made by the user via user interface 224, and may either transmit the selection or the selected parameter set to IMD 120 via telemetry circuitry 228 to deliver therapy according to the selected parameter set. Where programmer 220 stores parameter sets in memory 230, processor 222 may receive parameter sets from another programmer via input/output module 226 during programming by a clinician. For example, a patient programmer may receive parameter sets from a clinician programmer.

Telemetry module 228 may include a transceiver for wireless communication, appropriate ports for wired communication or communication via removable electrical media, or appropriate drives for communication via removable magnetic or optical media. If wireless communication is used, telemetry module 228 may support both wireless communication with IMD 120 and wireless communication with another programmer.

Similar to telemetry module 126 of IMD 120, telemetry module 228 operates as a transceiver for transmitting and receiving signals to and from IMD 120 and possibly another programmer. The receiver portion of telemetry module 228 includes a chopper mixer telemetry circuit, as described in this disclosure, producing a baseband signal that can be processed to recover the transmitted signal. In addition, telemetry module 126 includes a transmitter.

Power source 232 provides power to programmer 220. That is, power source 232 provides power to processor 222, user interface 224, input/output module 226, telemetry module 228, and memory 230. Because the linear micropower amplifier in telemetry module 228 operates at very low power, the life of power source 232 may be increased.

Power source 232 may take the form of a small, rechargeable or non-rechargeable battery, or an inductive power interface that transcutaneously receives inductively coupled energy. In the case of a rechargeable battery, power source 232 similarly may include an inductive power interface for transcutaneous transfer of recharge power.

Figure 9:
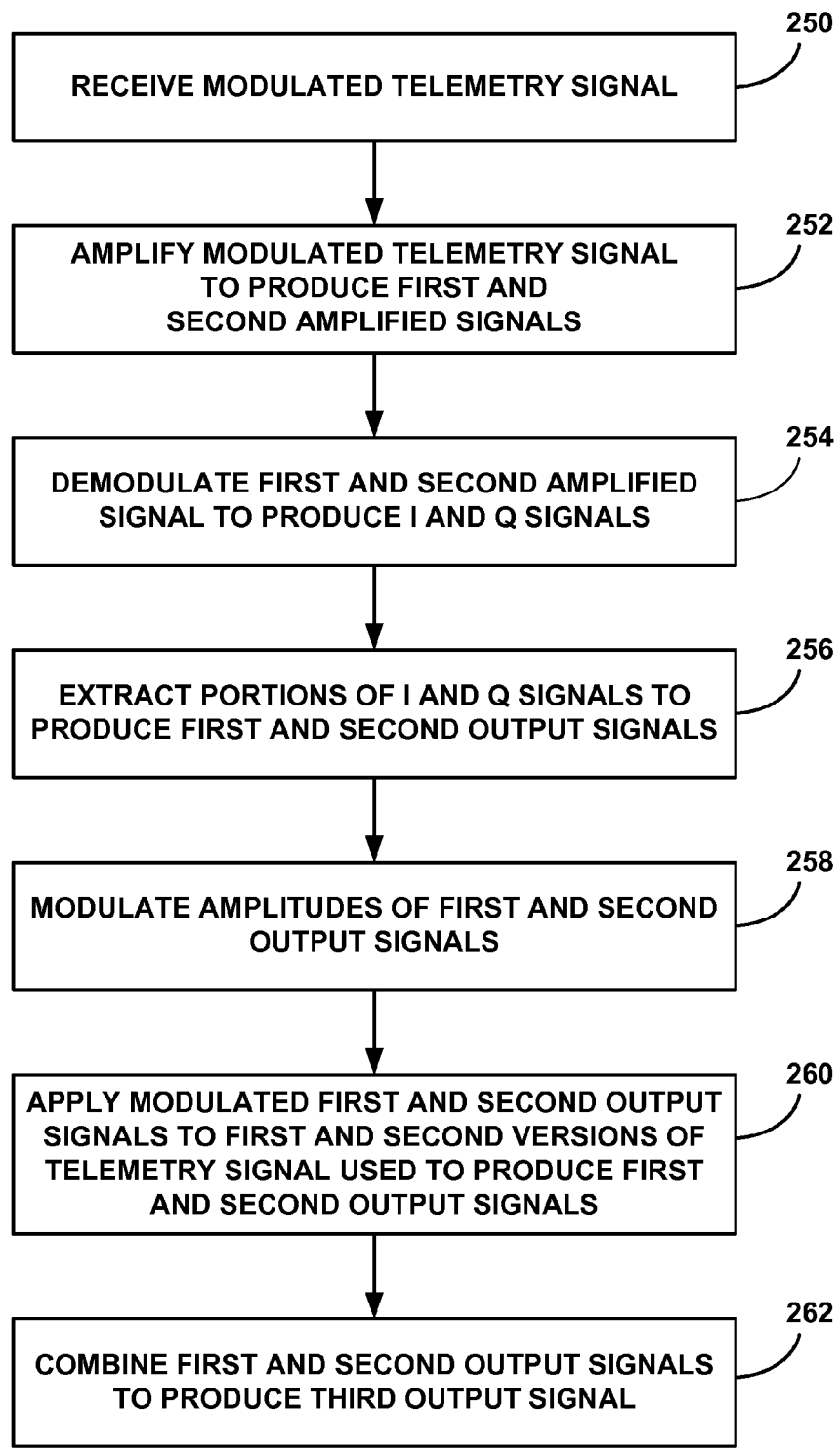
FIG. 9 is a flow diagram illustrating a method for wireless telemetry using a chopper mixer telemetry circuit.

FIG. 9 is a flow diagram illustrating a method for wireless telemetry using a chopper mixer telemetry circuit. The method shown in FIG. 9 may be implemented using circuitry as described in this disclosure. As shown in FIG. 9, a method may comprise receiving a wireless, modulated telemetry signal (250), amplifying the modulated telemetry signal to produce a first amplified signal and a second amplified signal (252), demodulating the first and second amplified signals at a common clock frequency, but 90 degrees phase shifted, to produce I and Q signal (254), extracting portions of the I and Q signals to produce first and second output signals (256), modulating the amplitudes of the first and second output signals (258), applying the first and second modulated output signals to the first and second versions of the modulated telemetry signal, respectively. used to produce the first and second output signals (260), and combining the first and second output signals to produce a third output signal (262). The third output signal then may be decoded.

Various embodiments of the invention have been described. These and other embodiments are within the scope of the following claims.

The invention claimed is:

1. A wireless receiver comprising:
a first mixer amplifier that receives a telemetry signal modulated at a clock frequency, amplifies the telemetry signal to produce a first amplified signal, demodulates the first amplified signal at the clock frequency to produce a first demodulated signal, and extracts a portion of the first demodulated signal to produce a first output signal;
a second mixer amplifier that receives the same telemetry signal as the first mixer amplifier, amplifies the telemetry signal to produce a second amplified signal, demodulates the second amplified signal at the clock frequency to produce a second demodulated signal that is approximately 90 degrees out of phase with the first demodulated signal, and extracts a portion of the second demodulated signal to produce a second output signal; and
circuitry that produces a third output signal based on the first and second output signals.

2. The receiver of claim 1, wherein the receiver resides within an implantable medical device.

3. The receiver of claim 2, wherein the implantable medical device includes one of a cardiac pacemaker, a cardiac defibrillator, an electrical neurostimulator, and an implantable drug delivery device.

4. The receiver of claim 1, wherein the first mixer amplifier includes a first integrator that integrates the first demodulated signal to extract the portion of the first demodulated signal to produce the first output signal, and wherein the second mixer amplifier includes a second integrator that integrates the second demodulated signal to extract the portion of the second demodulated signal to produce the second output signal.

5. The receiver of claim 1, wherein the circuitry comprises quadrature reconstruction circuitry that combines the first and second output signals to produce the third output signal, the third output signal being an amplified representation of the telemetry signal.

6. The receiver of claim 5, wherein the quadrature reconstruction circuitry comprises a first squaring unit that squares the first output signal, a second squaring unit that squares the second output signal, a summing unit that sums the squared first and second output signals, and a root unit that produces a square root of the sum as the third output signal.

7. The receiver of claim 6, further comprising a decoder that decodes the third output signal.

8. The receiver of claim 1, further comprising an antenna that receives the telemetry signal and presents the telemetry signal to the first and second mixer amplifiers.

9. A method comprising:
receiving a wireless, modulated telemetry signal;
amplifying the modulated telemetry signal to produce a first amplified signal;
demodulating the first amplified signal at a clock frequency to produce a first demodulated signal;
extracting a portion of the first demodulated signal to produce a first output signal;
amplifying the same modulated telemetry signal that was amplified to produce the first amplified signal to produce a second amplified signal;
demodulating the second amplified signal at the clock frequency to produce a second demodulated signal that is 90 degrees out of phase with the first demodulated signal;
extracting a portion of the second demodulated signal to produce a second output signal; and
producing a third output signal based on the first and second output signals.

10. The method of claim 8, further comprising receiving the wireless, modulated telemetry signal in an implantable medical device.

11. The method of claim 10, wherein the implantable medical device includes one of a cardiac pacemaker, a cardiac defibrillator, an electrical neurostimulator, and an implantable drug delivery device.

12. The method of claim 8, wherein extracting a portion of the first demodulated signal comprises integrating the first demodulated signal to produce the first output signal, and extracting a portion of the second demodulated signal comprises integrating the second demodulated signal to produce the second output signal.

13. The method of claim 8, wherein producing the third output signal based on the first and second output signals comprises:
combining the first and second output signals to produce the third output signal.

14. The method of claim 13, wherein combining the first and second output signals comprises squaring the first output signal, squaring the second output signal, summing the squared first and second output signals, and producing a square root of the sum as the third output signal.

15. The method of claim 14, further comprising decoding the third output signal.

16. The method of claim 8, further comprising receiving the telemetry signal via an antenna and presenting the telemetry signal to the first and second mixer amplifiers.

17. An apparatus comprising:
means for receiving a wireless, modulated telemetry signal;
means for amplifying the modulated telemetry signal to produce a first amplified signal;
means for demodulating the first amplified signal at a clock frequency to produce a first demodulated signal;
means for extracting a portion of the first demodulated signal to produce a first output signal;
means for amplifying the same modulated telemetry signal that was amplified to produce the first amplified signal to produce a second amplified signal;
means for demodulating the second amplified signal at the clock frequency to produce a second demodulated signal that is 90 degrees out of phase with the first demodulated signal;
means for extracting a portion of the second demodulated signal to produce a second output signal; and
means for producing a third output signal based on the first and second output signals.

18. The apparatus of claim 17, wherein the means for producing the third output signal comprises:
means for combining the first and second output signals to produce the third output signal.

19. The apparatus of claim 17, further comprising means for delivering medical therapy.

20. The apparatus of claim 17, further comprising means for sensing one or more physiological conditions.

21. An implantable medical device (IMD) comprising:
a first mixer amplifier that receives a telemetry signal modulated at a clock frequency, amplifies the telemetry signal to produce a first amplified signal, demodulates the first amplified signal at the clock frequency to produce a first demodulated signal, and extracts a portion of the first demodulated signal to produce a first output signal;
a second mixer amplifier that receives the same telemetry signal as the first mixer amplifier, amplifies the telemetry signal to produce a second amplified signal, demodulates the second amplified signal at the clock frequency to produce a second demodulated signal that is approximately 90 degrees out of phase with the first demodulated signal, and extracts a portion of the second demodulated signal to produce a second output signal; and
quadrature reconstruction circuitry that combines the first and second output signals to produce a third output signal, the third output signal being an amplified representation of the telemetry signal.

22. The IMD of claim 21, further comprising:
a first modulator that modulates an amplitude of the first output signal at the clock frequency;
a second modulator that modulates an amplitude of the second output signal at the clock frequency;
a first feedback path that applies the first modulated output signal as a first feedback signal to the first mixer amplifier; and
a second feedback path that applies the second modulated output signal as a second feedback signal to the second mixer amplifier.

23. The IMD of claim 22,
wherein the first mixer amplifier includes first and second differential inputs, and the second mixer amplifier includes first and second differential inputs,
wherein the first feedback path includes a first feedback path branch coupled to the first input of the first mixer amplifier and a second feedback path branch coupled to the second input of the first mixer amplifier, and
wherein the second feedback path includes a third feedback path branch coupled to the first input of the second mixer amplifier and a fourth feedback path branch coupled to the second input of the second mixer amplifier.

24. The IMD of claim 23,
wherein the first modulator includes a modulator in the first feedback path branch and a modulator in the second feedback path branch that modulate the amplitude of the first output signal out of phase with each other, and
wherein the second modulator includes a modulator in the third feedback path branch and a modulator in the fourth feedback path branch that modulate the amplitude of the second output signal out of phase with each other.

25. The IMD of claim 24,
wherein each of the first and second feedback path branches includes a first feedback capacitance, each of the first and second inputs of the first mixer amplifier is coupled to receive the telemetry signal via a first input capacitance, and a gain of the first mixer amplifier is at least partially dependent on a ratio of the first feedback capacitance to the first input capacitance, and
wherein each of the third and fourth feedback path branches includes a second feedback capacitance, each of the first and second inputs of the second mixer amplifier is coupled to receive the telemetry signal via a second input capacitance, and a gain of the second mixer amplifier is at least partially dependent on a ratio of the second feedback capacitance to the second input capacitance.

26. The IMD of claim 21, wherein the IMD includes one of a cardiac pacemaker, a cardiac defibrillator, an electrical neurostimulator, and an implantable drug delivery device.

27. The IMD of claim 21, wherein the first mixer amplifier includes a first integrator that integrates the first demodulated signal to extract the portion of the first demodulated signal to produce the first output signal, and wherein the second mixer amplifier includes a second integrator that integrates the second demodulated signal to extract the portion of the second demodulated signal to produce the second output signal.

28. The IMD of claim 21, wherein the quadrature reconstruction circuitry comprises a first squaring unit that squares the first output signal, a second squaring unit that squares the second output signal, a summing unit that sums the squared first and second output signals, and a root unit that produces a square root of the sum as the third output signal.

29. The IMD of claim 28, further comprising a decoder that decodes the third output signal.

30. The IMD of claim 21, further comprising an antenna that receives the telemetry signal and presents the telemetry signal to the first and second mixer amplifiers.

* * * * *